United States Patent
Yun et al.

(10) Patent No.: US 11,062,116 B2
(45) Date of Patent: Jul. 13, 2021

(54) ELECTRONIC DEVICE INCLUDING A PLURALITY OF LIGHT EMITTING UNITS AND A PLURALITY OF LIGHT RECEIVING UNITS

(71) Applicant: Samsung Electronics Co., Ltd., Suwon-si (KR)

(72) Inventors: Inho Yun, Suwon-si (KR); Yongjin Lee, Seoul (KR); Hyunseok Shin, Seongnam-si (KR); Jongho Park, Seoul (KR); Seungeun Lee, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 16/173,704

(22) Filed: Oct. 29, 2018

(65) Prior Publication Data

US 2019/0130156 A1 May 2, 2019

(30) Foreign Application Priority Data

Nov. 1, 2017 (KR) .......................... 10-2017-0144432

(51) Int. Cl.
*G06K 9/00* (2006.01)
*G16H 10/60* (2018.01)
(Continued)

(52) U.S. Cl.
CPC .......... *G06K 9/0004* (2013.01); *A61B 5/0059* (2013.01); *A61B 5/14551* (2013.01);
(Continued)

(58) Field of Classification Search
CPC ............. G06K 9/0004; G06K 9/00087; G06K 2009/0006; G16H 10/60; G16H 40/63; A61B 5/0059; A61B 5/14551; A61B 5/4872; A61B 5/7207; A61B 5/165; A61B 5/441

See application file for complete search history.

(56) References Cited

U.S. PATENT DOCUMENTS 9,392,946 B1    7/2016  Sarantos et al.
9,552,525 B2 *  1/2017  Breznicky .......... G06K 9/00067
(Continued)

FOREIGN PATENT DOCUMENTS

EP         3136954 A2    3/2017
JP      2014076273 A     5/2014
(Continued)

OTHER PUBLICATIONS

ISA/KR, "International Search Report," International Application No. PCT/KR2018/012730, dated Mar. 7, 2019, 4 pages.
(Continued)

*Primary Examiner* — Antonio Xavier

(57) ABSTRACT

An electronic device includes a light emitting unit, including a first light emitting element and a second light emitting element; and a plurality of light receiving units disposed in a structure that encloses the light emitting unit, wherein the first light emitting element and the second light emitting element are disposed in a separated state based on a radiation area related to the light emitting unit in a designated distance range. Various embodiments are available.

14 Claims, 24 Drawing Sheets

(51) Int. Cl.
 *A61B 5/00* (2006.01)
 *G16H 40/63* (2018.01)
 *A61B 5/1455* (2006.01)
 *A61B 5/16* (2006.01)

(52) U.S. Cl.
 CPC .......... *A61B 5/4872* (2013.01); *A61B 5/7207* (2013.01); *G06K 9/00087* (2013.01); *G16H 10/60* (2018.01); *G16H 40/63* (2018.01); *A61B 5/165* (2013.01); *A61B 5/441* (2013.01); *G06K 2009/0006* (2013.01)

(56) References Cited

U.S. PATENT DOCUMENTS

| | | | |
|---|---|---|---|
| 9,730,644 B1 | 8/2017 | Wu et al. | |
| 2008/0180950 A1* | 7/2008 | Kang | A61B 5/441 |
| | | | 362/249.16 |
| 2012/0083705 A1* | 4/2012 | Yuen | G16H 20/30 |
| | | | 600/508 |
| 2013/0035570 A1* | 2/2013 | Miyasato | A61B 5/14551 |
| | | | 600/323 |
| 2013/0217979 A1 | 8/2013 | Blackadar et al. | |
| 2014/0081153 A1 | 3/2014 | Kuno | |
| 2014/0197965 A1 | 7/2014 | Park et al. | |
| 2014/0275850 A1* | 9/2014 | Venkatraman | G01S 19/19 |
| | | | 600/301 |
| 2015/0324566 A1* | 11/2015 | Miura | G06K 9/00067 |
| | | | 726/19 |
| 2016/0029898 A1* | 2/2016 | LeBoeuf | A61B 5/7207 |
| | | | 600/301 |
| 2016/0058374 A1 | 3/2016 | Matsuno et al. | |
| 2016/0143584 A1* | 5/2016 | Inagaki | A61B 5/02416 |
| | | | 600/300 |
| 2016/0150978 A1* | 6/2016 | Yuen | A61B 5/681 |
| | | | 600/301 |
| 2016/0183818 A1 | 6/2016 | Richards et al. | |
| 2016/0206215 A1* | 7/2016 | Takahashi | A61B 5/681 |
| 2016/0206251 A1 | 7/2016 | Kwon et al. | |
| 2016/0241757 A1* | 8/2016 | Cheng | A61B 5/7203 |
| 2016/0361020 A1* | 12/2016 | LeBoeuf | A61B 5/721 |
| 2016/0374621 A1 | 12/2016 | LeBoeuf et al. | |
| 2017/0000350 A1 | 1/2017 | Kwon et al. | |
| 2017/0100038 A1* | 4/2017 | Narusawa | A61B 5/681 |
| 2017/0163948 A1* | 6/2017 | Morisawa | G06T 5/00 |
| 2018/0035907 A1* | 2/2018 | Park | A61B 5/7203 |
| 2018/0129121 A1* | 5/2018 | Van Der Sijde | H01L 33/502 |
| 2018/0353134 A1* | 12/2018 | Walter | A61B 5/02416 |

FOREIGN PATENT DOCUMENTS

| | | |
|---|---|---|
| JP | 2016047073 A | 4/2016 |
| JP | 2016154928 A | 9/2016 |
| JP | 6066451 B2 | 1/2017 |
| JP | 2017169690 A | 9/2017 |
| KR | 10-2016-0088127 A | 7/2016 |

OTHER PUBLICATIONS

Supplementary Partial European Search Report dated Oct. 8, 2020 in connection with European Application No. 18874652.3, 9 pages.
Supplementary European Search Report dated Mar. 2, 2021 in connection with European Application No. 18874652.3, 10 pages.

* cited by examiner

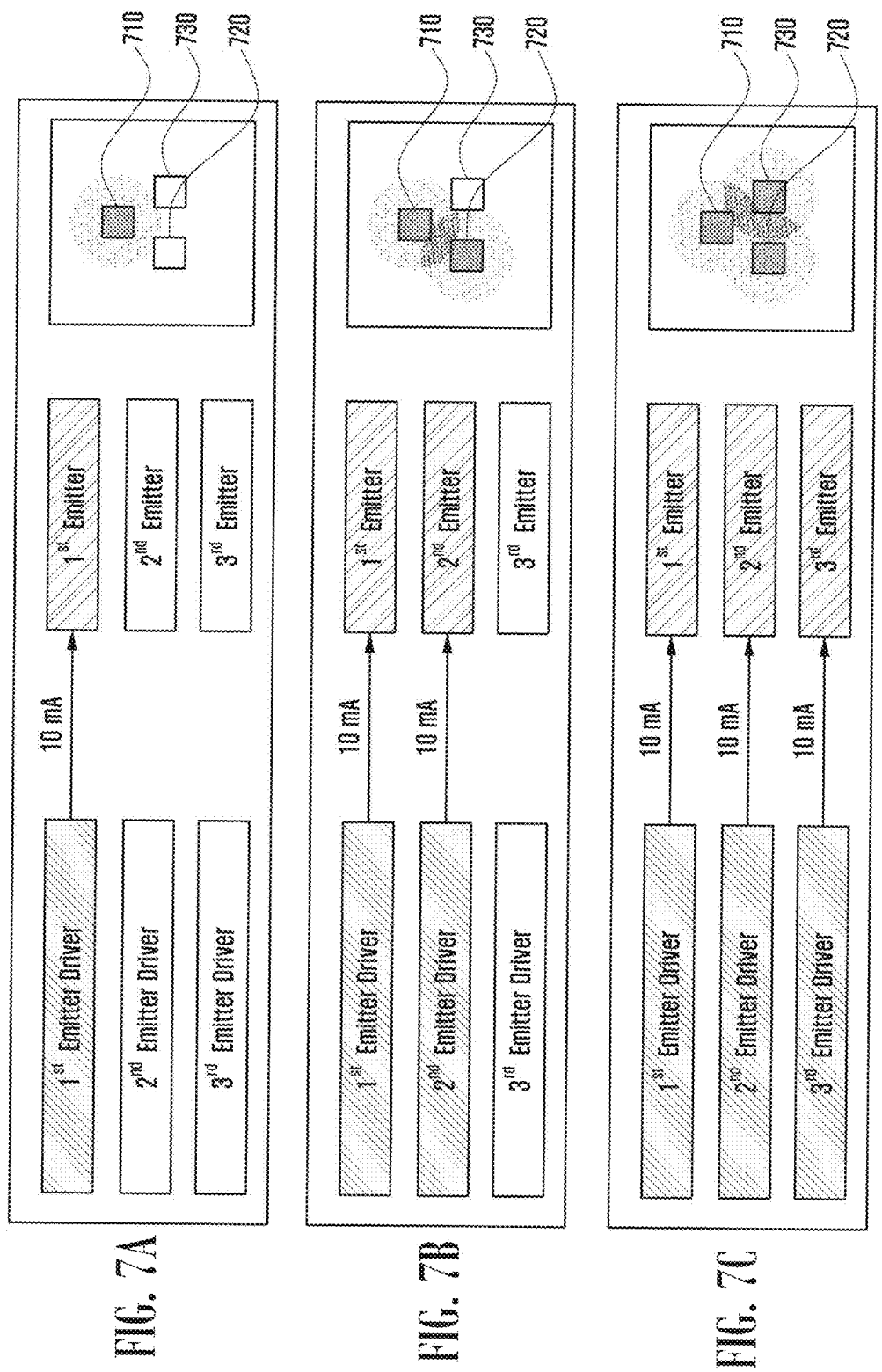

FIG. 18
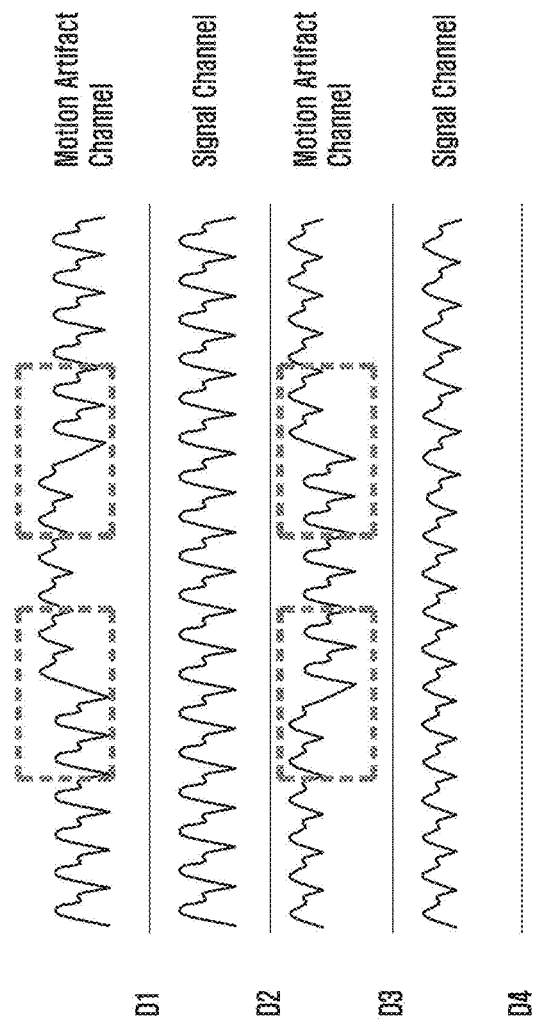
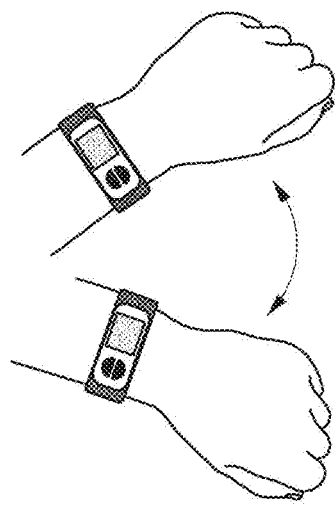

ELECTRONIC DEVICE INCLUDING A PLURALITY OF LIGHT EMITTING UNITS AND A PLURALITY OF LIGHT RECEIVING UNITS

CROSS-REFERENCE TO RELATED APPLICATION

This application is based on and claims priority under 35 U.S.C. § 119 to Korean Patent Application No. 10-2017-0144432, filed on Nov. 1, 2017, in the Korean Intellectual Property Office, the disclosure of which is incorporated by reference herein in its entirety.

BACKGROUND

1. Field

The present disclosure relates to an electronic device including a plurality of light emitting units and a plurality of light receiving units.

2. Description of the Related Art

With the remarkable development of information communication technology and semiconductor technology, spread and use of electronic devices are rapidly increasing. These electronic devices have a trend to converge and provide various functions without staying in their respective traditional areas. For example, the electronic device may include various sensors such as an optical sensor, acceleration sensor, and electrode sensor.

The electronic device may measure a user's biometric signal using such various sensors and provide biometric information of the user. For example, the electronic device may provide various bio information such as a heart rate, the number of steps, a sleeping state, stress information, body fat information, and a calorie consumption amount of a user.

In recent years, wearable electronic devices have been developed to measure biometric signals in a user's exercise time or daily life and are used for recording activities and monitoring a change in biorhythms and health information.

SUMMARY

The present disclosure provides an electronic device for determining a ratio of light absorbed into the blood upon emitting light by directly contacting an optical sensor included therein with a user's skin and calculating the user's body information based on the absorbed light ratio.

However, when a biometric signal is measured using an optical sensor in a user's exercise time or daily life, motion artifact according to the user's motion may be included in the biometric signal. Further, while the optical sensor indirectly contacts (e.g., occurrence of a separation phenomenon) the user's skin, peripheral noise (e.g., ambient light) may be included in the biometric signal.

In order to remove such noise, the electronic device may obtain operation information using an acceleration sensor and select a structure of disposing a light emitting unit at a periphery of a light receiving unit of the optical sensor. However, these methods may not accurately determine and remove peripheral noise or motion artifact.

In accordance with an aspect of the present disclosure, an electronic device includes a light emitting unit including a first light emitting element and a second light emitting element; and a plurality of light receiving units disposed in a structure that encloses the light emitting unit, wherein the first light emitting element and the second light emitting element are disposed in a separated state based on a radiation area related to the light emitting unit in a designated distance range.

In accordance with another aspect of the present disclosure, an electronic device includes a light emitting unit including a plurality of first light emitting elements configured to output first light having a first wavelength; at least one light receiving unit; and a processor, wherein the processor is configured to determine reception of a request for obtaining a biometric signal corresponding to a living body; to select at least one first light emitting element of the plurality of first light emitting elements based on at least some of user information related to the living body, when the request is received; to control the light emitting unit to output light through the at least one selected first light emitting element; to control the at least one light receiving unit to obtain at least some of light reflected by the living body among the output light; and to detect the biometric signal based on at least some of the obtained light.

In accordance with another aspect of the present disclosure, an electronic device includes a light emitting unit including at least one first light emitting element configured to output first light having a first wavelength and at least one second light emitting element configured to output second light having a second wavelength; at least one light receiving unit; and a processor, wherein the processor is configured to determine reception of a request for obtaining a biometric signal corresponding to a living body, to determine a wavelength of light based on at least some of user information related to the living body, when the request is received; to select one or more light emitting elements of the at least one first light emitting element and the at least one second light emitting element based on the determined light wavelength; to control the light emitting unit to output light through the one or more selected light emitting elements; to control the at least one light receiving unit to obtain at least some of light reflected by the living body among the output light, and to detect the biometric signal based on at least some of the obtained light.

In accordance with another aspect of the present disclosure, an electronic device includes a first light receiving unit; a second light receiving unit; a light emitting unit disposed between the first light receiving unit and the second light receiving unit and including at least one light emitting element; and a processor functionally connected to the first light receiving unit, the second light receiving unit, and the light emitting unit, wherein the processor is configured to determine reception of a request for obtaining a biometric signal corresponding to a living body, to control the light emitting unit to output light, when the request is received, to control the first light receiving unit and the second light receiving unit to obtain at least some of light reflected by the living body among the output light, to detect the first biometric signal based on at least some of the light obtained by the first light receiving unit, to detect the second biometric signal based on at least some of the light obtained by the second light receiving unit, to compare the first biometric signal and the second biometric signal to determine whether noise has occurred, and to determine the biometric signal based on whether the determined noise has occurred.

Before undertaking the DETAILED DESCRIPTION below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware or software, or some combination of at least two of the same. It should be noted that the functionality associated with any particular controller may be centralized or distributed, whether locally or remotely.

Moreover, various functions described below can be implemented or supported by one or more computer programs, each of which is formed from computer readable program code and embodied in a computer readable medium. The terms "application" and "program" refer to one or more computer programs, software components, sets of instructions, procedures, functions, objects, classes, instances, related data, or a portion thereof adapted for implementation in a suitable computer readable program code. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), or any other type of memory. A "non-transitory" computer readable medium excludes wired, wireless, optical, or other communication links that transport transitory electrical or other signals. A non-transitory computer readable medium includes media where data can be permanently stored and media where data can be stored and later overwritten, such as a rewritable optical disc or an erasable memory device.

Definitions for certain words and phrases are provided throughout this patent document. Those of ordinary skill in the art should understand that in many, if not most instances, such definitions apply to prior, as well as future uses of such defined words and phrases.

BRIEF DESCRIPTION OF THE DRAWINGS

The objects, features, and advantages of the present disclosure will be more apparent from the following detailed description in conjunction with the accompanying drawings, in which:

FIGS. 7A-7C are diagrams illustrating an example in which an electronic device adjusts an intensity of light according to various embodiments;

FIGS. 15-18 are graphs and diagrams illustrating examples in which an electronic device determines motion artifact according to various embodiments.

DETAILED DESCRIPTION

Figure 1:
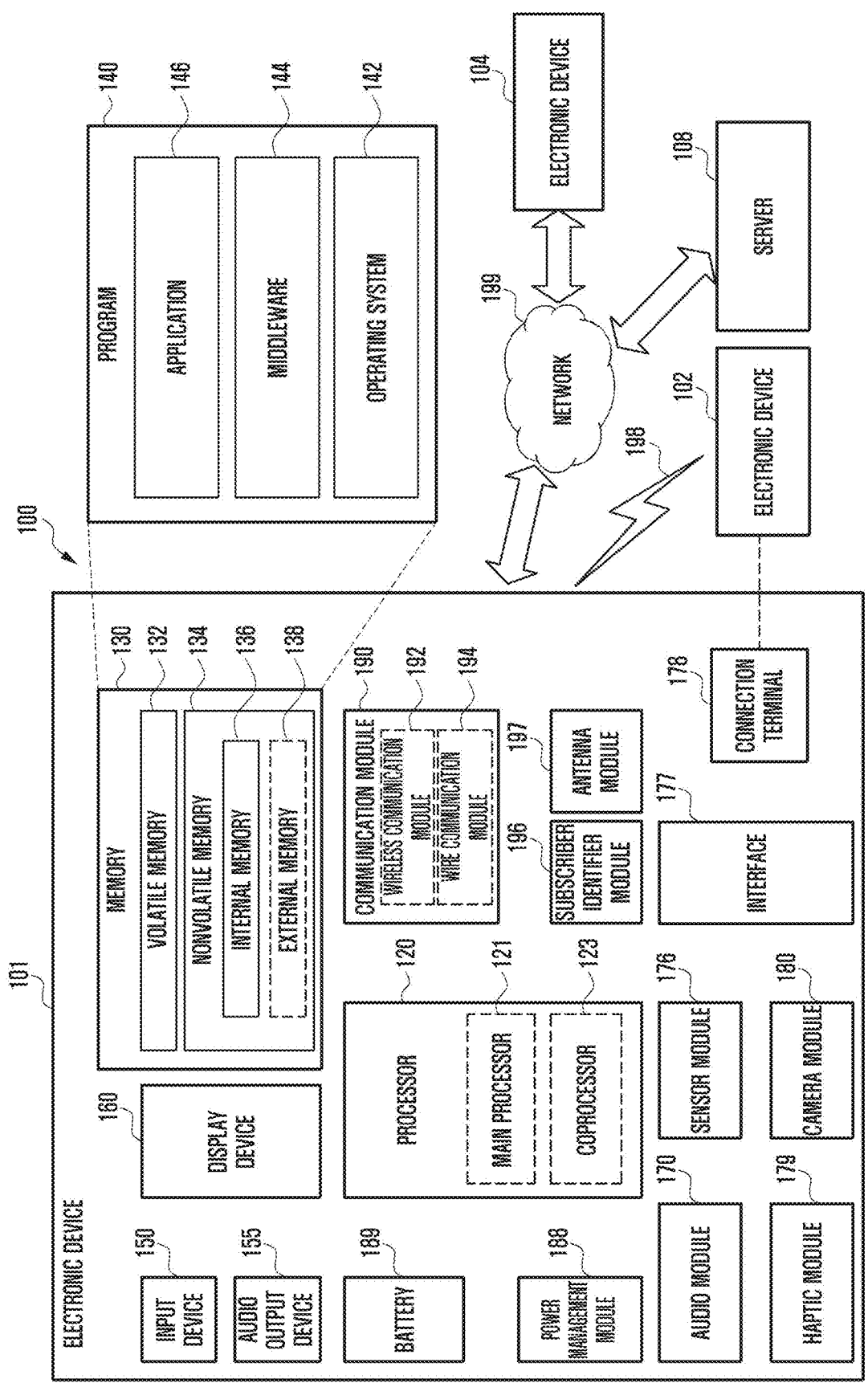
FIG. 1 is a block diagram illustrating a configuration of an electronic device in a network environment including a plurality of light emitting units and a plurality of light receiving units according to various embodiments.

FIGS. 1 through 19B, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged system or device FIG. 1 is a block diagram illustrating an electronic device 101 in a network environment 100 according to various embodiments. Referring to FIG. 1, the electronic device 101 in the network environment 100 may communicate with an electronic device 102 via a first network 198 (e.g., a short-range wireless communication network), or an electronic device 104 or a server 108 via a second network 199 (e.g., a long-range wireless communication network). According to an embodiment, the electronic device 101 may communicate with the electronic device 104 via the server 108. According to an embodiment, the electronic device 101 may include a processor 120, memory 130, an input device 150, a sound output device 155, a display device 160, an audio module 170, a sensor module 176, an interface 177, a haptic module 179, a camera module 180, a power management module 188, a battery 189, a communication module 190, a subscriber identification module (SIM) 196, or an antenna module 197. In some embodiments, at least one (e.g., the display device 160 or the camera module 180) of the components may be omitted from the electronic device 101, or one or more other components may be added in the electronic device 101. In some embodiments, some of the components may be implemented as single integrated circuitry. For example, the sensor module 176 (e.g., a fingerprint sensor, an iris sensor, or an illuminance sensor) may be implemented as embedded in the display device 160 (e.g., a display).

The processor 120 may execute, for example, software (e.g., a program 140) to control at least one other component (e.g., a hardware or software component) of the electronic device 101 coupled with the processor 120, and may perform various data processing or computation. According to one embodiment, as at least part of the data processing or computation, the processor 120 may load a command or data received from another component (e.g., the sensor module 176 or the communication module 190) in volatile memory 132, process the command or the data stored in the volatile memory 132, and store resulting data in non-volatile memory 134. According to an embodiment, the processor 120 may include a main processor 121 (e.g., a central processing unit (CPU) or an application processor (AP)), and an auxiliary processor 123 (e.g., a graphics processing unit (GPU), an image signal processor (ISP), a sensor hub processor, or a communication processor (CP)) that is operable independently from, or in conjunction with, the main processor 121. Additionally or alternatively, the auxiliary processor 123 may be adapted to consume less power than the main processor 121, or to be specific to a specified function. The auxiliary processor 123 may be implemented as separate from, or as part of the main processor 121.

The auxiliary processor 123 may control at least some of functions or states related to at least one component (e.g., the display device 160, the sensor module 176, or the communication module 190) among the components of the electronic device 101, instead of the main processor 121 while the main processor 121 is in an inactive (e.g., sleep) state, or together with the main processor 121 while the main processor 121 is in an active state (e.g., executing an application). According to an embodiment, the auxiliary processor 123 (e.g., an image signal processor or a communication processor) may be implemented as part of another component (e.g., the camera module 180 or the communication module 190) functionally related to the auxiliary processor 123.

The memory 130 may store various data used by at least one component (e.g., the processor 120 or the sensor module 176) of the electronic device 101. The various data may include, for example, software (e.g., the program 140) and input data or output data for a command related thererto. The memory 130 may include the volatile memory 132 or the non-volatile memory 134.

The program 140 may be stored in the memory 130 as software, and may include, for example, an operating system (OS) 142, middleware 144, or an application 146.

The input device 150 may receive a command or data to be used by other component (e.g., the processor 120) of the electronic device 101, from the outside (e.g., a user) of the electronic device 101. The input device 150 may include, for example, a microphone, a mouse, a keyboard, or a digital pen (e.g., a stylus pen).

The sound output device 155 may output sound signals to the outside of the electronic device 101. The sound output device 155 may include, for example, a speaker or a receiver. The speaker may be used for general purposes, such as playing multimedia or playing record, and the receiver may be used for an incoming calls. According to an embodiment, the receiver may be implemented as separate from, or as part of, the speaker.

The display device 160 may visually provide information to the outside (e.g., a user) of the electronic device 101. The display device 160 may include, for example, a display, a hologram device, or a projector and control circuitry to control a corresponding one of the display, hologram device, and projector. According to an embodiment, the display device 160 may include touch circuitry adapted to detect a touch, or sensor circuitry (e.g., a pressure sensor) adapted to measure the intensity of force incurred by the touch.

The audio module 170 may convert a sound into an electrical signal and vice versa. According to an embodiment, the audio module 170 may obtain the sound via the input device 150, or output the sound via the sound output device 155 or a headphone of an external electronic device (e.g., an electronic device 102) directly (e.g., wiredly) or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. According to an embodiment, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly (e.g., wiredly) or wirelessly. According to an embodiment, the interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102). According to an embodiment, the connecting terminal 178 may include, for example, a HDMI connector, a USB connector, a SD card connector, or an audio connector (e.g., a headphone connector).

The haptic module 179 may convert an electrical signal into a mechanical stimulus (e.g., a vibration or a movement) or electrical stimulus which may be recognized by a user via his tactile sensation or kinesthetic sensation. According to an embodiment, the haptic module 179 may include, for example, a motor, a piezoelectric element, or an electric stimulator.

The camera module 180 may capture a still image or moving images. According to an embodiment, the camera module 180 may include one or more lenses, image sensors, image signal processors, or flashes.

The power management module 188 may manage power supplied to the electronic device 101. According to one embodiment, the power management module 188 may be implemented as at least part of, for example, a power management integrated circuit (PMIC).

The battery 189 may supply power to at least one component of the electronic device 101. According to an embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more communication processors that are operable independently from the processor 120 (e.g., the application processor (AP)) and supports a direct (e.g., wired) communication or a wireless communication. According to an embodiment, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device via the first network 198 (e.g., a short-range communication network, such as Bluetooth™, wireless-fidelity (Wi-Fi) direct, or infrared data association (IrDA)) or the second network 199 (e.g., a long-range communication network, such as a cellular network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 192 may identify and authenticate the electronic device 101 in a communication network, such as the first network 198 or the second network 199, using subscriber information (e.g., international mobile subscriber identity (IMSI)) stored in the subscriber identification module 196.

The antenna module 197 may transmit or receive a signal or power to or from the outside (e.g., the external electronic device) of the electronic device 101. According to an embodiment, the antenna module 197 may include an antenna including a radiating element composed of a conductive material or a conductive pattern formed in or on a substrate (e.g., PCB). According to an embodiment, the antenna module 197 may include a plurality of antennas. In such a case, at least one antenna appropriate for a communication scheme used in the communication network, such as the first network 198 or the second network 199, may be selected, for example, by the communication module 190 (e.g., the wireless communication module 192) from the plurality of antennas. The signal or the power may then be transmitted or received between the communication module 190 and the external electronic device via the selected at least one antenna. According to an embodiment, another component (e.g., a radio frequency integrated circuit (RFIC)) other than the radiating element may be additionally formed as part of the antenna module 197.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 101 and the external electronic device 104 via the server 108 coupled with the second network 199. Each of the electronic devices 102 and 104 may be a device of a same type as, or a different type, from the electronic device 101. According to an embodiment, all or some of operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, or client-server computing technology may be used, for example.

Figure 2:
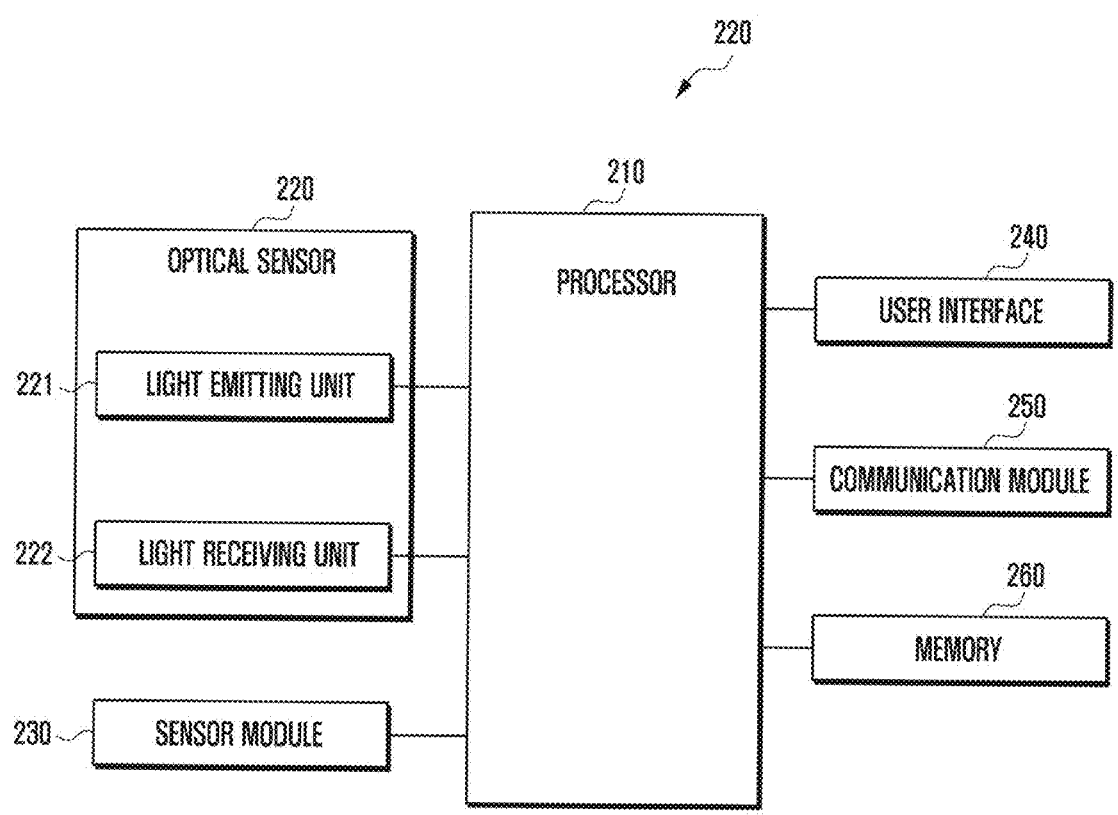
FIG. 2 is a block diagram illustrating a configuration of an electronic device according to various embodiments.

FIG. 2 is a block diagram illustrating a configuration of an electronic device according to various embodiments.

According to various embodiments, an electronic device 200 (e.g., the electronic device 101 of FIG. 1) may include one or more processors 210 (e.g., the processor 120 of FIG. 1), an optical sensor 220, a sensor module 230 (e.g., the sensor module 176 of FIG. 1), a user interface 240, a communication module 250 (e.g., the communication module 190 of FIG. 1), and a memory 260 (the memory 130 of FIG. 1). In some embodiments, the electronic device 200 may omit at least one of the components or may additionally have other components.

The processor 210 may include at least one of a central processing unit (CPU), an application processor, and a communications processor (CP). The processor 210 may, for example, perform operations or data processing related to the control and/or communication of at least one other component of the electronic device 200.

The optical sensor 220 may include at least one light emitting unit 221 and at least one light receiving unit 222.

The light emitting unit 221 may be configured to output light and/or an intensity of the selected light. The light emitting unit 221 may include, for example, a plurality of light emitting elements and may be configured to select at least one light emitting element of the plurality of light emitting elements to output light. According to various embodiments, the plurality of light emitting elements may be configured to output light of the same wavelength or different wavelengths. For example, the plurality of light emitting elements may be configured to output light having a wavelength of at least one of blue light, green light, yellow light, red light, and infrared light. The plurality of light emitting elements may be distinguished according to an output wavelength band. The processor 210 may adjust an intensity of an electric current supplied to the light emitting elements to adjust an intensity of output light.

The light receiving unit 222 is a device for measuring an intensity of spectral light and may change and measure an amount of applied photons to a current. For example, the light receiving unit 222 may include a photodiode and a pyroelectric detector. The electronic device 200 may include, for example, a plurality of light receiving units 222. The plurality of light receiving units 222 may be connected to a plurality of analog-digital converters in a form of a multiplexer and may control to switch the plurality of light receiving units 222 according to a situation to obtain one signal or a plurality of signals. For example, the electronic device 200 may determine that a user's motion is small to, for example, during sleep and control to connect the plurality of light receiving units to one analog-to-digital converter to obtain one signal. In some embodiments, the processor 210 of the electronic device 200 may determine that a user's motion is large to, for example, during exercise and control to connect the plurality of light receiving units 222 to a plurality of analog-to-digital converters to obtain a plurality of signals. When a plurality of signals are obtained, the processor 210 of the electronic device 200 may compare the plurality of obtained signals with each other and select a signal determined to be less affected by noise or correct a signal based on determined noise.

The sensor module 230 may include at least one of, for example, a gesture sensor, gyro sensor, atmospheric pressure sensor, magnetic sensor, acceleration sensor, grip sensor, proximity sensor, color sensor, infrared (IR) sensor, biometric sensor, temperature sensor, humidity sensor, and illumination sensor. The sensor module 230 may determine situation information related to the electronic device 200. The sensor module 230 may be configured to determine at least one of, for example, motion information, exercise information, and position information of the user. The user interface 240 may include, for example, at least one of an input device, microphone, speaker, display, and camera.

The communication module 250 may include, for example, wireless communication or wired communication. Wireless communication may include cellular communication that uses at least one of, for example, long term evolution (LTE), LTE advance (LTE-A), code division multiple access (CDMA), wideband CDMA (WCDMA), universal mobile telecommunications system (UMTS), wireless broadband (WiBro), and global system for mobile communications (GSM). According to an embodiment, wireless communication may include, for example, at least one of wireless fidelity (WiFi), Bluetooth, Bluetooth low energy (BLE), Zigbee, near field communication (NFC), magnetic secure transmission, radio frequency (RF), and body area network (BAN). According to an embodiment, wireless communication may include a global navigation satellite system (GNSS). The GNSS may be, for example, a global positioning system (GPS), global navigation satellite system (Glonass), Beidou navigation satellite system (hereinafter "Beidou") or Galileo, and European global satellite-based navigation system. Hereinafter, in this document, the "GPS" may be interchangeably used with the "GNSS". Wired communication may include at least one of, for example, a universal serial bus (USB), a high definition multimedia interface (HDMI), recommended standard 232 (RS-232), power line communication, and a plain old telephone service (POTS).

The memory 260 may store one or more programs executed by the processor 210 and perform a function for temporary storage of input/output data. The input/output data may include, for example, data for controlling the light emitting unit 221 or the light receiving unit 222 and user information data related to a living body.

According to various embodiments of the present disclosure, the electronic device 200 includes a light emitting unit 221 including a plurality of first light emitting elements configured to output first light having a first wavelength; at least one light receiving unit 222; and a processor 210, wherein the processor 210 is configured to determine reception of a request for obtaining a biometric signal corresponding to a living body; and to select at least one first light emitting element of the plurality of first light emitting elements based on at least some of user information related to the living body, when the request is received; to control the light emitting unit 221 to output light through the at least one selected first light emitting element; to control the at least one light receiving unit 222 to obtain at least some of light reflected by the living body among the output light; and to detect the biometric signal based on at least some of the obtained light.

According to various embodiments of the present disclosure, each of the plurality of first light emitting elements of the electronic device 200 may have an output intensity of a designated range.

According to various embodiments of the present disclosure, the processor 210 of the electronic device 200 may be configured to select at least one first light emitting element having an output intensity of a designated range among the plurality of first light emitting elements based on at least some of user information related to the living body, when the request is received; and to control the light emitting unit 221 to output light through the at least one selected first light emitting element.

According to various embodiments of the present disclosure, the electronic device 200 may further include a user interface 240 configured to receive a user input, wherein the processor 210 may be configured to receive at least some of user information related to the living body using the user interface 240; to determine characteristics of the living body based on user information related to the living body; and to select at least one first light emitting element of the plurality of first light emitting elements based on at least the determined characteristics of the living body.

According to various embodiments of the present disclosure, the electronic device 200 may further include a communication module 250 configured to perform data communication, wherein the processor 210 may be configured to receive at least some of user information related to the living body using the communication module 250; and to determine characteristics of the living body based on at least user information related to the living body; and to select at least one first light emitting element of the plurality of first light emitting elements based on at least the determined characteristic of the living body.

According to various embodiments of the present disclosure, the request for obtaining the biometric signal may be configured to occur based on occurrence of an event previously set by a user or an event according to a user's health state.

According to various embodiments of the present disclosure, the user information related to the living body may include at least one of user age, sex, genetic information, and hospital treatment history.

According to various embodiments of the present disclosure, the electronic device 200 may further include a sensor module 230 configured to determine situation information related thereto, wherein the processor 210 may be configured to control the sensor module 230 to determine the situation information; and to select at least one first light emitting element of the plurality of first light emitting elements based on at least the situation information.

According to various embodiments of the present disclosure, the situation information may include at least one of motion information, exercise information, and position information of a user.

According to various embodiments of the present disclosure, the processor 210 of the electronic device 200 may be configured to select at least one first light emitting element of the plurality of first light emitting elements based on at least information of the electronic device 200.

According to various embodiments of the present disclosure, information of the electronic device 200 may include at least one of battery information and information of a running application.

According to various embodiments, the electronic device 200 includes a light emitting unit 221 including at least one first light emitting element configured to output first light having a first wavelength and at least one second light emitting element configured to output second light having a second wavelength; at least one light receiving unit 222; and a processor 210, wherein the processor 210 is configured to determine reception of a request for obtaining a biometric signal corresponding to a living body, to determine a wavelength of light based on at least some of user information related to the living body, when the request is received; to select one or more light emitting elements of the at least one first light emitting element and the at least one second light emitting element based on the determined light wavelength; to control the light emitting unit 221 to output light through the at least one selected light emitting element; to control the at least one light receiving unit 222 to obtain at least some of light reflected by the living body among the output light, and to detect the biometric signal based on at least some of the obtained light.

According to various embodiments, in the electronic device 200, each of the at least one first light emitting element and the at least one second light emitting element may have an output intensity of a designated range.

According to various embodiments, the processor 210 of the electronic device 200 may further determine an intensity of light based on at least some of user information related to the living body, when the request is received; and to select one or more light emitting elements of the at least one first light emitting element and the at least one second light emitting element based on the determined light wavelength and the light intensity.

According to various embodiments, the electronic device 200 may include a first light receiving unit; a second light receiving unit; a light emitting unit 221 disposed between the first light receiving unit and the second light receiving unit and including at least one light emitting element; and a processor 210 functionally connected to the first light receiving unit, the second light receiving unit, and the light emitting unit, wherein the processor 210 is configured to determine reception of a request for obtaining a biometric signal corresponding to a living body, to control the light emitting unit to output light, when the request is received, to control the first light receiving unit and the second light receiving unit to obtain at least some of light reflected by the living body among the output light, to detect a first biometric signal based on at least some of the light obtained by the first light receiving unit, to detect a second biometric signal based on at least some of the light obtained by the second light receiving unit, to compare the first biometric signal and the second biometric signal to determine whether noise has occurred, and to determine the biometric signal based on whether the determined noise has occurred.

According to various embodiments, the noise may include at least one of motion artifact and peripheral noise.

According to various embodiments, the electronic device 200 may further include a sensor module configured to detect a moving state thereof, wherein the processor may be configured to determine the moving state of the electronic device using the sensor module 230; and to determine whether the motion artifact has occurred based on the determined moving state of the electronic device.

According to various embodiments, the processor 210 of the electronic device 200 may be configured to remove the predicted motion artifact from at least one of the first biometric signal and the second biometric signal.

According to various embodiments, the processor 210 of the electronic device 200 may be configured to select a biometric signal determined to be less affected by noise among the first biometric signal and the second biometric signal and to perform correction that removes the determined noise from at least one of the first biometric signal and the second biometric signal based on at least the selection.

Figure 3:
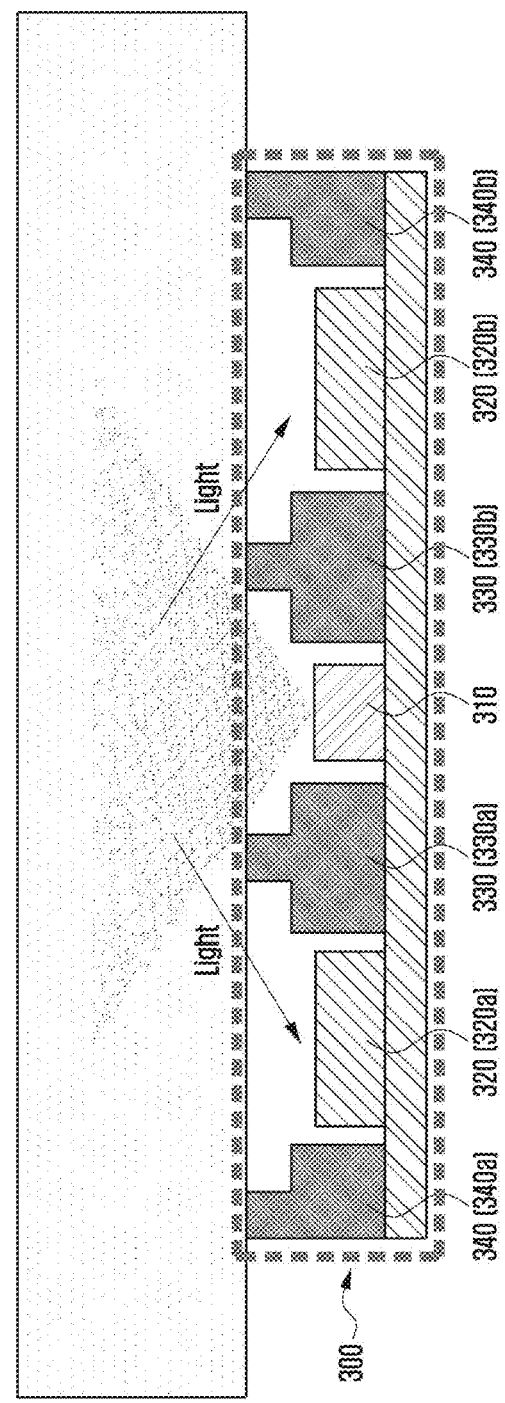
FIG. 3 is a cross-sectional view illustrating a structure of an optical sensor according to various embodiments.

FIG. 3 is a cross-sectional view illustrating a structure of an optical sensor according to various embodiments.

According to various embodiments, an optical sensor 300 may include at least one light emitting unit 310 (e.g., the light emitting unit 221 of FIG. 2), at least one light receiving unit 320 (e.g., the light receiving unit 222 of FIG. 2), a first barrier rib 330, and a second barrier rib 340. In various embodiments, the optical sensor 300 may omit at least one of the components or may additionally include other components.

According to various embodiments, the light emitting unit 310 of the optical sensor 300 may include at least one light emitting element. For example, the light emitting unit 310 may include a plurality of first light emitting elements for outputting first light having a first wavelength. As another example, the light emitting unit 310 may include at least one first light emitting element for outputting first light having a first wavelength and at least one second light emitting element for outputting second light having a second wavelength.

According to various embodiments, the light receiving unit 320 of the optical sensor 300 is a device that measures an intensity of spectral light and may change and measure an amount of applied photons to a current. For example, the light receiving unit 320 may control to obtain at least some of light reflected by the living body among light output by the light emitting unit 310. According to an embodiment, the optical sensor 300 may include at least two light receiving units 320 (e.g., a light receiving unit 320a and a light receiving unit 320b). For example, the optical sensor 300 may be formed in a structure in which at least two light receiving units 320 enclose the light emitting unit 310.

A structure in which at least two light receiving units 320 enclose the light emitting unit 310 may reduce a loss of light output from the light emitting unit 310. For example, light output by the light emitting unit 310 may form a radiation area having a predetermined radius. The radiation area may include, for example, at least an area in which the light emitting unit 310 is disposed and may be larger than an area in which the light emitting unit 310 is disposed. Accordingly, in order to cover the radiation area, at least two light receiving units 320 may enclose the light emitting unit 310. Further, because the generally used light receiving unit 320 is formed with a passive device, the difference in power consumption may not be large even if the light receiving unit 320 is used frequently. A structure in which at least two light receiving units 320 enclose the light emitting unit 310 may have the advantage of being able to exhibit a similar performance even if the structure consumes a small amount of current, compared with a structure in which at least two light emitting units 310 enclose the light receiving unit 320. Further, according to the structure in which at least two light receiving units 320 enclose the light emitting unit 310, the light emitting unit 310 may be disposed at a periphery of a central portion of the optical sensor 300. Such a structure may prevent light from leaking through some space between the user and the optical sensor. For example, even if the optical sensor emits light in a dark place, a light path may be blocked by the user's skin or a wall of the electronic device; thus, light may not be leaked.

According to various embodiments, in order to prevent light output from the light emitting unit 310 or light around the optical sensor 300 from being directly applied to the light receiving unit 320, the optical sensor 300 may further include a first barrier rib 330 and/or a second barrier rib 340. According to various embodiments, the optical sensor 300 may include first barrier ribs 330 (e.g., a first barrier rib 330a and a first barrier rib 330b) disposed between the light receiving unit 320 and the light emitting unit 310. For example, when some of light output from the light emitting unit 310 are directly applied to the light receiving unit 320 without passing through the living body, the optical sensor 300 may detect an inaccurate biometric signal. As another example, when light is reflected by a surface of the optical sensor 300 or a surface of the living body to be applied to the light receiving unit 320, biometric information is not included in incident light; thus, an inaccurate biometric signal may be detected. Accordingly, by disposing the first barrier ribs 330 (e.g., the first barrier rib 330a and the first barrier rib 330b) between the light receiving unit 320 and the light emitting unit 310, light output from the light emitting unit 310 may be prevented from being directly applied to the light receiving unit 320 without passing through the living body. According to various embodiments, in order to prevent light around the optical sensor 300 from being directly applied to the light receiving unit 320, the optical sensor 300 may include second barrier ribs 340 (e.g., a second barrier rib 340a and a second barrier rib 340b) disposed between the light receiving unit 320 and an external environment. According to various embodiments, shapes of the barrier ribs (e.g., the first barrier rib 330 or the second barrier rib 340) may be formed in various shapes according to the purpose of the barrier ribs, a structure of the device, and the like.

Figure 4A:
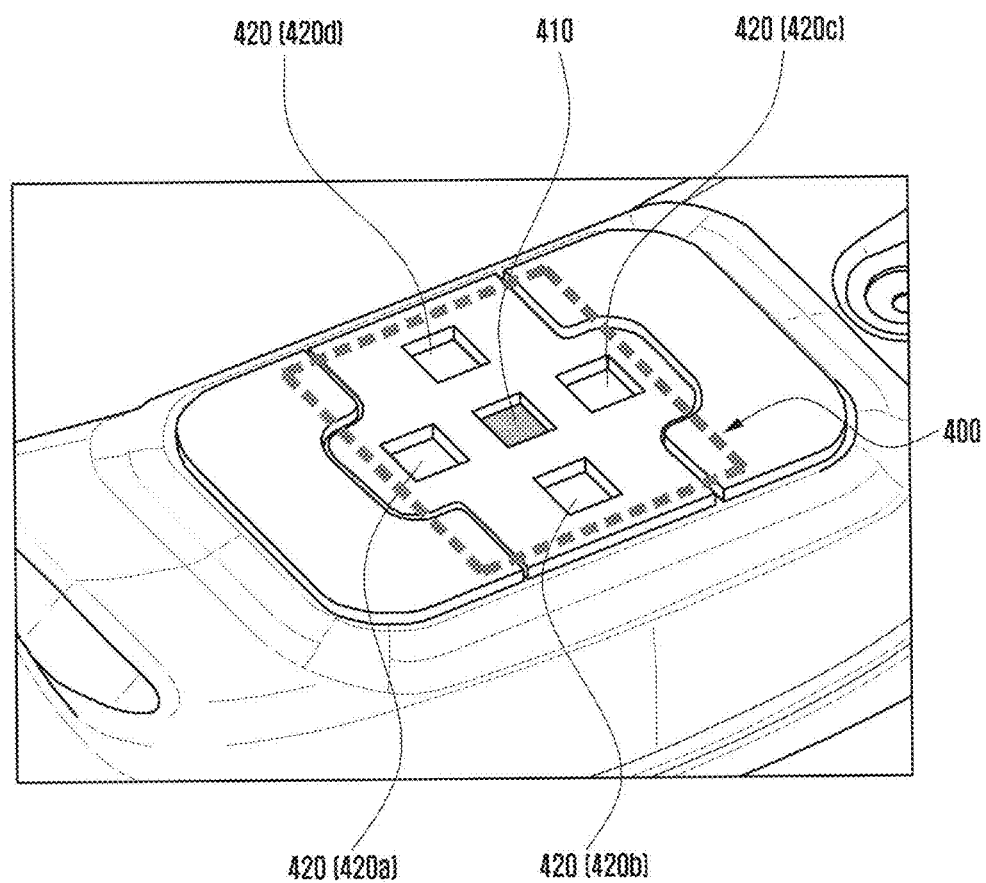
FIGS. 4A and 4B are diagrams illustrating an outer shape of an electronic device including an optical sensor according to various embodiments.
Figure 4B:
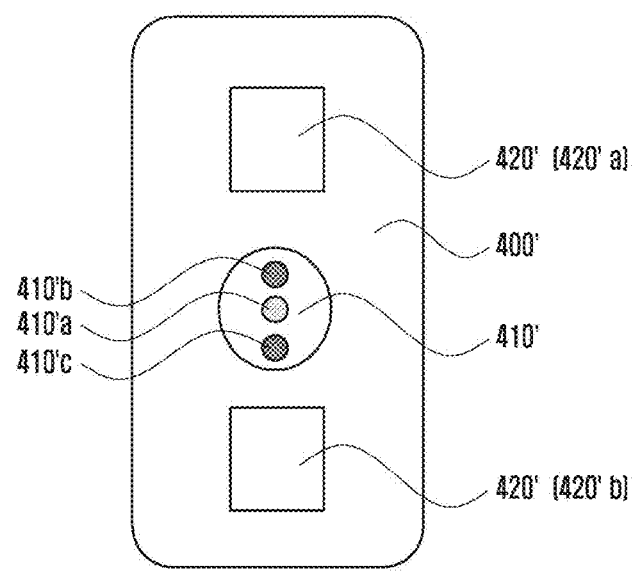

FIGS. 4A and 4B are diagrams illustrating an outer shape of an electronic device including an optical sensor 400 according to various embodiments.

With reference to FIG. 4A, the optical sensor 400 may include at least one light emitting unit 410 and a plurality of light receiving units 420. The plurality of light receiving units may be disposed in a shape enclosing at least one light emitting unit 410. For example, a plurality of light receiving units (e.g., a first light receiving unit 420a, second light receiving unit 420b, third light receiving unit 420c, and fourth light receiving unit 420d) on a virtual circle enclosing the light emitting unit 410 may be disposed apart from each other by a predetermined distance. Although FIG. 4A illustrates a case in which the optical sensor 400 includes four light receiving units, various embodiments of the present disclosure are not limited thereto.

With reference to FIG. 4B, an optical sensor 400' may include a light emitting unit 410' including a plurality of light emitting elements and a plurality of light receiving units 420'. The plurality of light receiving units (e.g., a first light receiving unit 420'a and a second light receiving unit 420'b) may be disposed in a shape that encloses the light emitting unit 410'. Further, the light emitting unit 410' may include a plurality of light emitting elements. For example, a first light emitting element 410'a may be configured to output first light having a first wavelength, and a second light emitting element 410'b may be configured to output second light having a second wavelength.

In various embodiments, the light emitting unit 410' may further include a third light emitting element 410'c. As another example, the light emitting unit 410' may include a plurality of light emitting elements (e.g., a first light emitting element 410'a, second light emitting element 410'b, and third light emitting element 410'c) that output light of the same wavelength. Although FIG. 4B illustrates a case in which the light emitting unit 410' includes three light emitting elements, various embodiments of the present disclosure are not limited thereto.

Figures 5A, 5B:
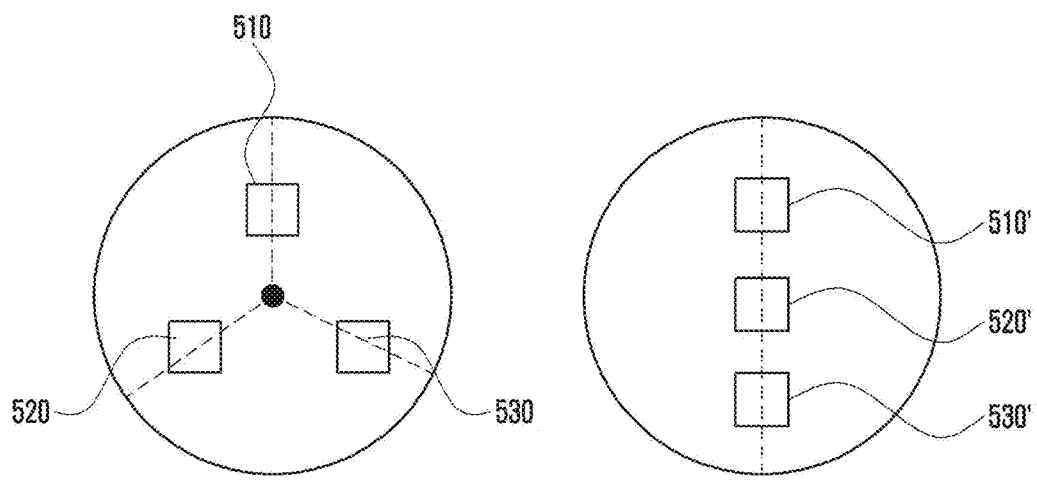
FIGS. 5A and 5B are diagrams illustrating a disposition structure of light emitting elements according to various embodiments.

FIGS. 5A and 5B are diagrams illustrating a disposition structure of a plurality of light emitting elements of a light emitting unit according to various embodiments.

According to various embodiments, the light emitting unit may include three or more light emitting elements. When the number of the light emitting elements is three or more, the light emitting unit may mount light emitting elements in a various disposition structure.

For example, FIG. 5A illustrates that a plurality of light emitting elements (e.g., a first light emitting element 510, second light emitting element 520, and third light emitting element 530) may be disposed with a predetermined gap and a predetermined angle based on a central point.

In various embodiments, the structure may be used when each of the plurality of light emitting elements is a light emitting element having the same wavelength band. In various embodiments, when each of the plurality of light emitting elements of the structure simultaneously outputs light of the same wavelength band, a wider radiation area may be formed than when one light emitting element forms a radiation area. This method may have higher power efficiency than when using one light emitting element. For example, by adjusting the number of light emitting elements that output light according to a situation, it is possible to have higher light efficiency than that when using only one light emitting element. However, it does mean to be able to use a disposition structure illustrated in FIG. 5A only when a plurality of light emitting elements have the same wavelength. For example, when disposing the first light emitting element 510 having a wavelength corresponding to red light, the second light emitting element 520 having a wavelength corresponding to green light, and the third light emitting element 530 having a wavelength corresponding to blue light, as illustrated in FIG. 5A, by combining lights output from each light emitting element, light of a desired wavelength band may be generated.

As another example, the first light emitting element 510 and the second light emitting element 520 may have a wavelength corresponding to green light, and the third light emitting element 530 may have a wavelength corresponding to red light.

FIG. 5B illustrates that a plurality of light emitting elements (e.g., a first light emitting element 510', second light emitting element 520', and third light emitting element 530') may be spaced apart by a predetermined distance on a virtual line. Such a structure may be used when each of the plurality of light emitting elements outputs light of different wavelength bands. For example, the first light emitting element 510' may be configured to output first light having a first wavelength, and the second light emitting element 520' and the third light emitting element 530' may be configured to output second light having a second wavelength. However, this does not mean that a disposition structure illustrated in FIG. 5B may be used only when a plurality of light emitting elements are different. For example, by disposing the first light emitting element 510', the second light emitting element 520', and the third light emitting element 530' that output the same wavelength band, as illustrated in FIG. 5B and by configuring each thereof to have different emission angles, an external loss of output light may be reduced.

Figure 6A:
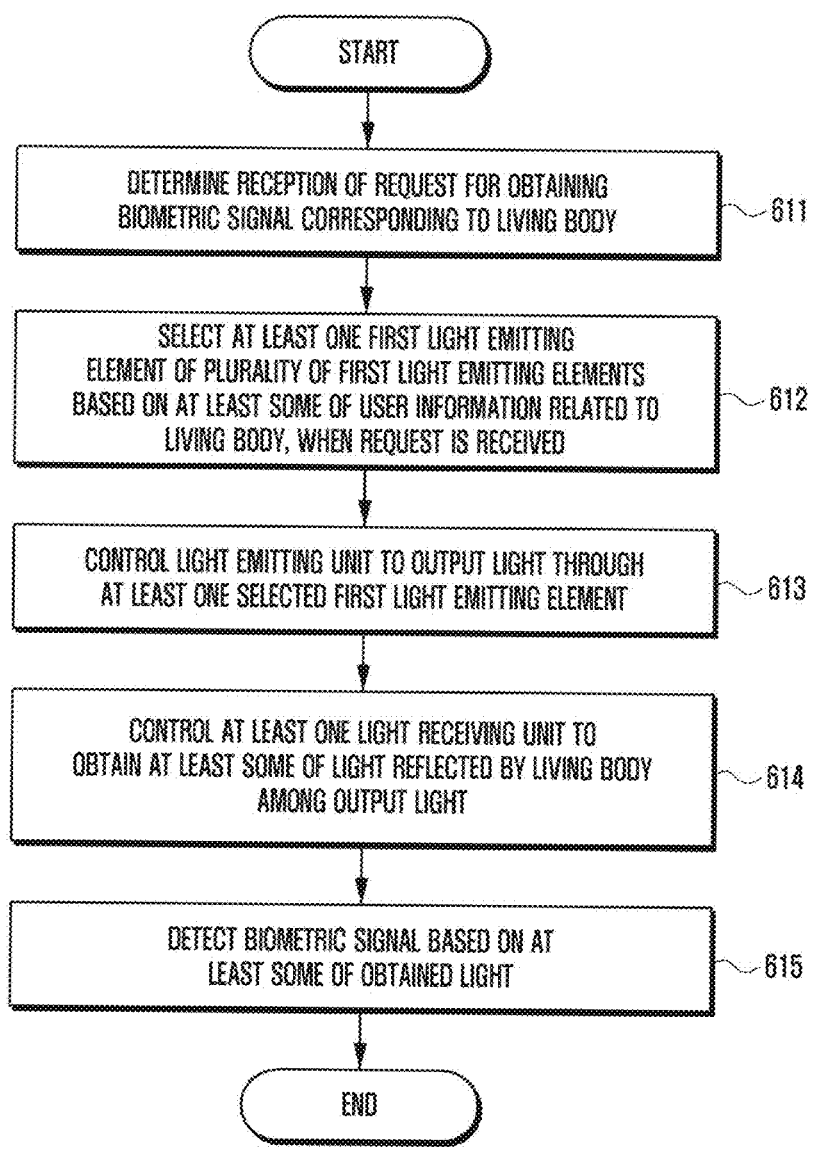
FIGS. 6A and 6B are flowcharts illustrating a method of controlling an electronic device including an optical sensor according to various embodiments.
Figure 6B:
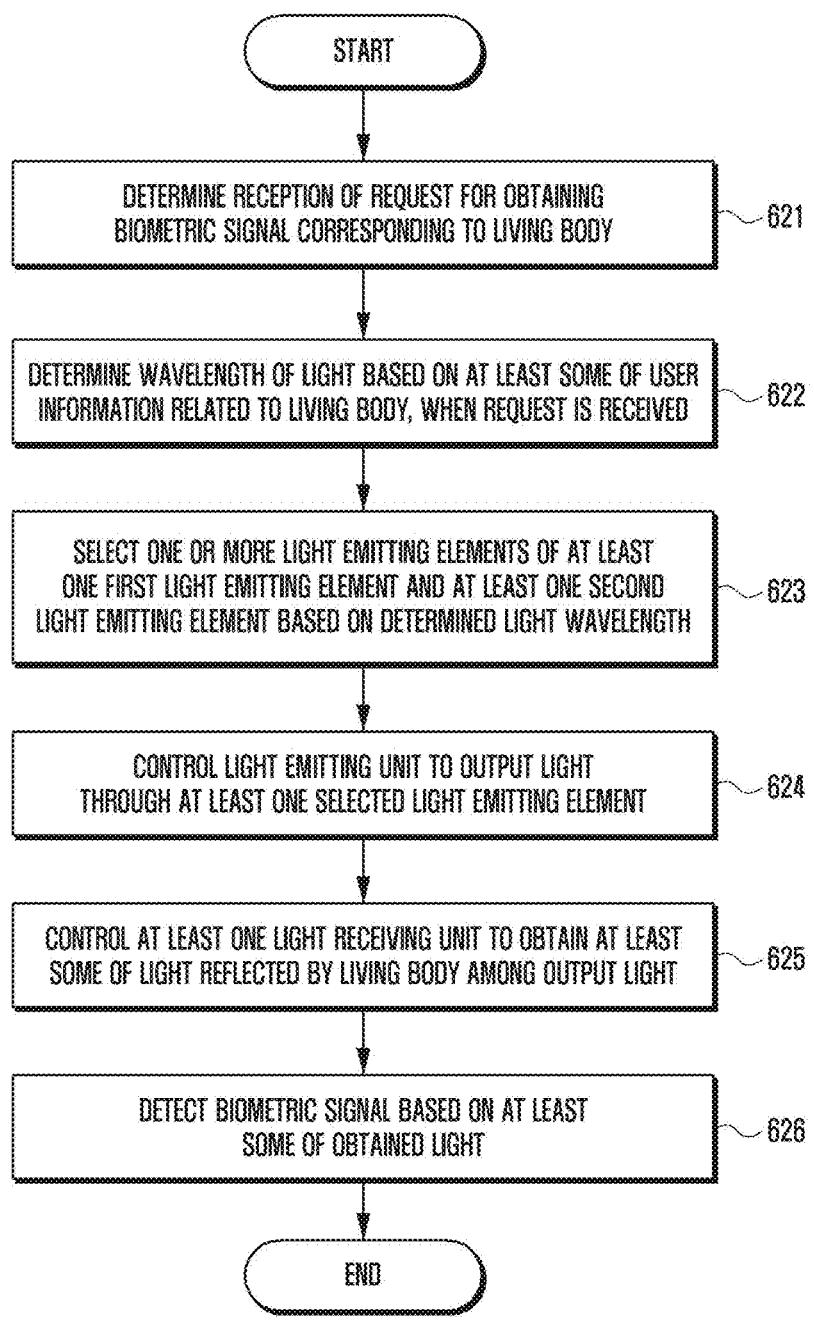

FIGS. 6A and 6B are flowcharts illustrating a method of controlling an electronic device including an optical sensor according to various embodiments.

FIG. 6A illustrates a control method when an optical sensor of an electronic device includes a plurality of first light emitting elements for outputting first light having a first wavelength.

With reference to FIG. 6A, at operation 611, the processor 210 of the electronic device 200 may determine reception of a request for obtaining a biometric signal corresponding to a living body.

According to various embodiments, a biometric signal corresponding to a living body may be related to at least one biometric information of a heart rate, stress index, blood oxygen saturation, maximum heart rate, body fat, local body fat, skin tone, melanin, wrinkle, skin moisture, blood sugar, and blood pressure.

According to various embodiments, a request for obtaining a biometric signal corresponding to a living body may be received based on a user command or a pre-designated schedule. According to an embodiment, a request for obtaining a biometric signal may be received based on occurrence of an event previously set by the user or an event according to a health state of the user. According to an embodiment, the processor 210 may receive a request for obtaining a biometric signal from an external device through a communication module.

A case based on a user command may include, for example, when the user executes an application related to biometric signal obtainment, when receiving a user input for activating an optical sensor, or when receiving a request for a user's biometric signal from an external device through a communication module.

A case based on a pre-designated schedule may include, for example, a case of determining biometric information according to a predetermined period or a case in which continuous determination of biometric information is used.

At operation 612, when the request is received, the processor 210 of the electronic device 200 may select at least one first light emitting element of the plurality of first light emitting elements based on at least some of user information related to the living body.

According to various embodiments, the memory 260 of the electronic device 200 may store user information related to a living body, including at least one of user age, sex, genetic information, and hospital treatment history. For example, the processor 210 of the electronic device 200 may determine at least one of a user's skin tone, blood pressure, blood sugar amount, heart rate, blood oxygen saturation, stress index, and body fat index based on the stored user information and determine an intensity or a radiation range of light necessary for obtaining the requested biometric signal. For example, a case of a user having a bright skin tone may be determined to output light of a lower intensity than that of a case of a user having a non-bright skin tone (e.g., a dark skin tone).

According to various embodiments, each of the plurality of first light emitting elements may be configured to have an output intensity of a designated range. For example, each of the plurality of first light emitting elements may be configured with light emitting elements having an output intensity of 50 mA. In this case, the processor 210 may determine an intensity or a radiation range of light necessary for obtaining the requested biometric signal and select at least one first light emitting element of the first light emitting elements having the same output intensity. As another example, each of the plurality of first light emitting elements may include light emitting elements having different output intensities such as 20 mA, 30 mA, or 50 mA. In this case, the processor 210 may determine an intensity or a radiation range of light necessary for obtaining the requested biometric signal and select at least one light emitting element of the plurality of first light emitting elements having different output intensities according to the determined light intensity or radiation range.

According to various embodiments, the processor 210 of the electronic device 200 may receive at least some of user information related to the living body using the user interface 240, determine characteristics of the living body based on at least user information related to the living body, and select at least one first light emitting element of the plurality of first light emitting elements based on at least the determined living body characteristics. For example, the user may directly input user information related to the user's living body through an input device.

According to various embodiments, the processor 210 of the electronic device 200 may receive at least some of user information related to the living body using the communication module 250, determine characteristics of the living body based on at least user information related to the living body, and select at least one first light emitting element of the plurality of first light emitting elements based on at least the determined living body characteristics.

According to various embodiments, the processor 210 of the electronic device 200 may determine situation information related to the electronic device 200 using the sensor module 230 and select at least one first light emitting element of the plurality of first light emitting elements based on the situation information. The situation information may include, for example, at least one of the user's motion information, exercise information, and position information.

According to various embodiments, the processor 210 of the electronic device 200 may select at least one first light emitting element of the plurality of first light emitting elements based on information of the electronic device 200. The information of the electronic device 200 may include, for example, at least one of battery information and information of a running application.

At operation 613, the processor 210 of the electronic device 200 may control the light emitting unit to output light through the at least one selected first light emitting element.

For example, in order to output light through the at least one selected first light emitting element, the processor 210 of the electronic device 200 may supply a current of a necessary intensity to the at least one selected first light emitting element.

At operation 614, the processor 210 of the electronic device 200 may control at least one light receiving unit to obtain at least some of light reflected by the living body among the output light.

When the light emitting unit of the optical sensor directly contacts the user's skin and outputs light, the light is diffused within the user's skin. Diffused light undergoes actions such as absorption, reflection, or scattering by a cell, pigment, venous blood, or arterial blood, and some light may be again output outside the skin. At least one light receiving unit may be used for obtaining some of the light output outside the skin.

At operation 615, the processor 210 of the electronic device 200 may detect the biometric signal based on at least some of the obtained light.

The biometric signal, for example, some of light output outside the skin may include at least one of a direct current (DC) component returned to a predetermined size by a skin, tissue, pigment, etc., a venous blood DC by absorption or reflection of venous blood of capillaries, an arterial blood DC component by absorption or reflection of arterial blood of capillaries, and an AC component by arterial blood.

According to various embodiments, the processor 210 of the electronic device 200 may convert biometric signals detected through predetermined algorithm to biometric information. For example, the detected biometric signal may be converted to at least one biometric information of a heart rate, stress index, blood oxygen saturation, maximum heart rate, body fat, local body fat, skin tone, melanin, wrinkles, skin moisture, blood sugar, and blood pressure to be displayed through a user interface or transferred to an external device.

FIG. 6B illustrates a control method when an optical sensor of an electronic device includes at least one first light emitting element for outputting first light having a first wavelength and at least one second light emitting element for outputting second light having a second wavelength.

With reference to FIG. 6B, at operation 621, the processor 210 of the electronic device 200 may determine reception of a request for obtaining a biometric signal corresponding to a living body. For example, the processor 210 may perform substantially the same operation as operation 611 of FIG. 6A.

At operation 622, when receiving the request, the processor 210 of the electronic device 200 may determine a wavelength of light based on at least some of user information related to the living body.

For example, when the user information related to the living body is related to a heart rate, a wavelength band corresponding to any one of green light, red light, and infrared light may be determined. As another example, when the user information related to the living body is related to oxygen saturation, a wavelength band corresponding to infrared light may be determined. As another example, when user information related to the living body is related to blood sugar, a wavelength band corresponding to blue light may be determined.

At operation 623, the processor 210 of the electronic device 200 may select one or more light emitting elements of the at least one first light emitting element and the at least one second light emitting element based on the determined light wavelength.

For example, when the wavelength of the determined light corresponds to first light, the processor 210 of the electronic device 200 may select one or more light emitting elements of at least one first light emitting element, and when the wavelength of the determined light corresponds to second light, the processor 210 of the electronic device 200 may select one or more light emitting elements of at least one second light emitting element. As another example, the processor 210 may determine that the wavelength of the determined light does not correspond to any one of the first light and the second light and select one or more light emitting elements of the at least one first light emitting element and the at least one second light emitting element in order to output a wavelength of the determined light by combining the first light and the second light.

At operation 624, the processor 210 of the electronic device 200 may control the light emitting unit to output light through the at least one selected light emitting element. For example, the processor 210 may perform substantially the same operations as operation 613 of FIG. 6A.

At operation 625, the processor 210 of the electronic device 200 may control at least one light receiving unit to obtain at least some of light reflected by the living body among the output light. For example, the processor 210 may perform substantially the same operation as operation 614 of FIG. 6A.

At operation 626, the processor 210 of the electronic device 200 may detect the biometric signal based on at least some of the obtained light. For example, the processor 210 may perform substantially the same operations as operation 615 of FIG. 6A.

FIGS. 7A-7C are diagrams illustrating an example in which an electronic device adjusts an intensity of light according to various embodiments.

According to various embodiments of the present disclosure, the light emitting unit of the optical sensor may include a plurality of first light emitting elements for outputting first light having a first wavelength.

FIG. 7A illustrates a case in which a current of 10 mA is supplied to a first light emitting element 710. For example, because an intensity of light necessary for measuring a heartbeat of a user having a bright skin tone may be smaller than that of a user having relatively different skin tones, light may be output by supplying a relatively small current. In a case of a user having a bright skin tone, even if only a current of 10 mA is supplied to the first light emitting element 710, a heartbeat waveform having a low signal-to-noise ratio may be obtained, similar to a case of supplying a current of 30 mA.

FIG. 7B illustrates a case in which 10 mA is supplied to a first light emitting element 710 and a second light emitting element 720. For example, it may mean an intensity of light used when outputting light toward a user with a medium skin tone. For example, an intensity of light necessary for measuring a heart rate of a user with a medium skin tone may be larger than a user with a relatively bright skin tone, but may be smaller than a user with a dark skin tone. Accordingly, when a current of 10 mA is supplied to each of the first light emitting element 710 and the second light emitting element 720, a heartbeat waveform having a low signal-to-noise ratio may be obtained. In this case, because a radiation area larger than a radiation area formed by supplying a current of 20 mA to one light emitting element may be formed, efficiency of heartbeat measurement may be improved.

FIG. 7C illustrates a case of supplying 10 mA to a first light emitting element 710, second light emitting element 720, and third light emitting element 730. For example, it may mean an intensity of light used when outputting light toward a user having a dark skin tone. Because it is possible to form a radiation area larger than a radiation area formed by supplying a current of 30 mA to one light emitting element, efficiency of heartbeat measurement may be improved.

Figure 8:
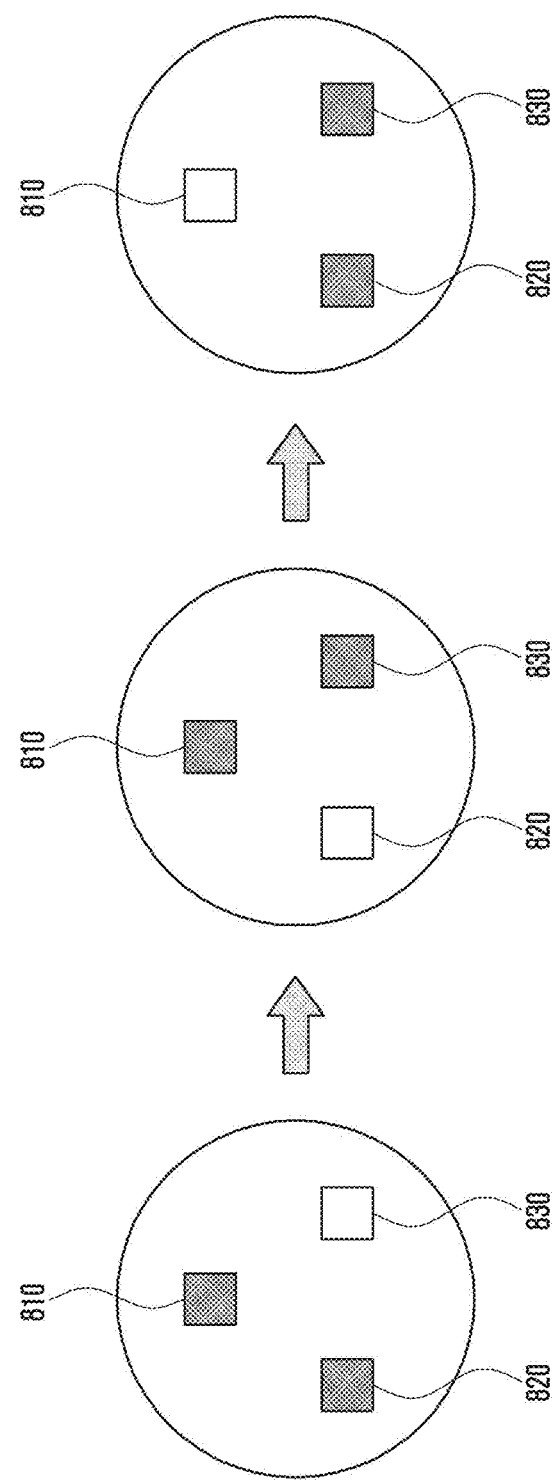
FIG. 8 is a diagram illustrating an example in which an electronic device constantly maintains an intensity of light according to various embodiments.

FIG. 8 is a diagram illustrating an example in which an electronic device constantly maintains an intensity of light according to various embodiments.

When continuous obtainment of a biometric signal is used, the light emitting unit may continuously output light. For example, when the user's continuous heart rate information is used, the light emitting unit may determine an intensity of light based on user information related to a living body and continuously output light to the living body based on the determined light intensity.

However, when only a specific light emitting element continuously outputs light, light emitting elements included in one light emitting unit may have the difference in performance and lifetime. In this case, a problem may occur in outputting light with the determined light intensity.

Therefore, the light emitting elements included in one light emitting unit may be used uniformly. For example, when it is determined that two light emitting elements output light, a first light emitting element 810 and a second light emitting element 820 output light and after a predetermined time has elapsed, the first light emitting element 810 and a third light emitting element 830 may be changed to output light. Further, after a predetermined time has elapsed, the second light emitting element 820 and the third light emitting element 830 may be changed to output light to uniformly use the light emitting elements included in one light emitting unit.

Figure 9A:
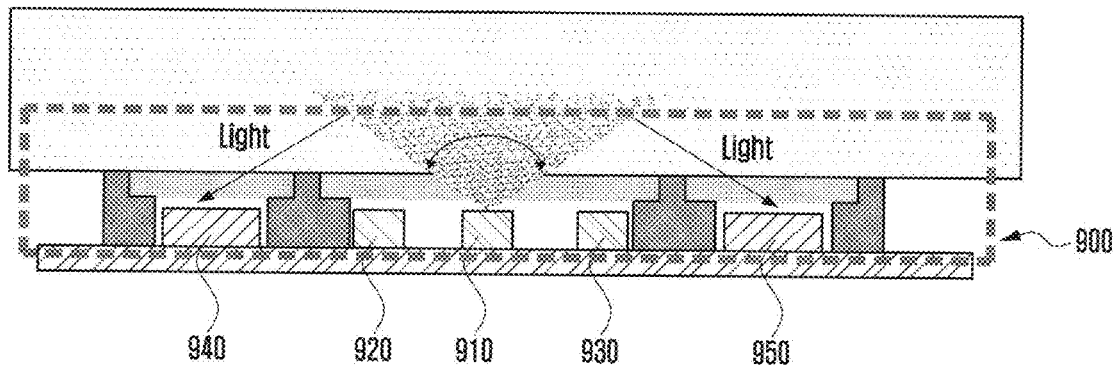
FIGS. 9A-9C are cross-sectional views illustrating a structure of an optical sensor according to various embodiments.
Figure 9B:
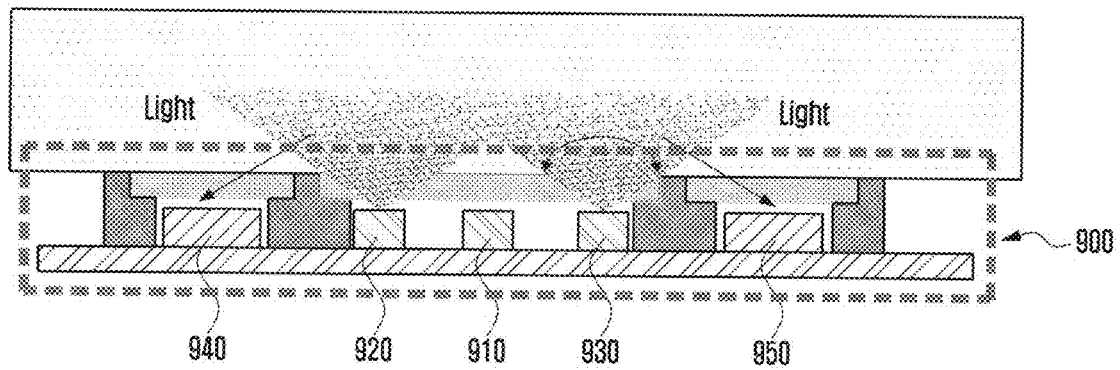
Figure 9C:
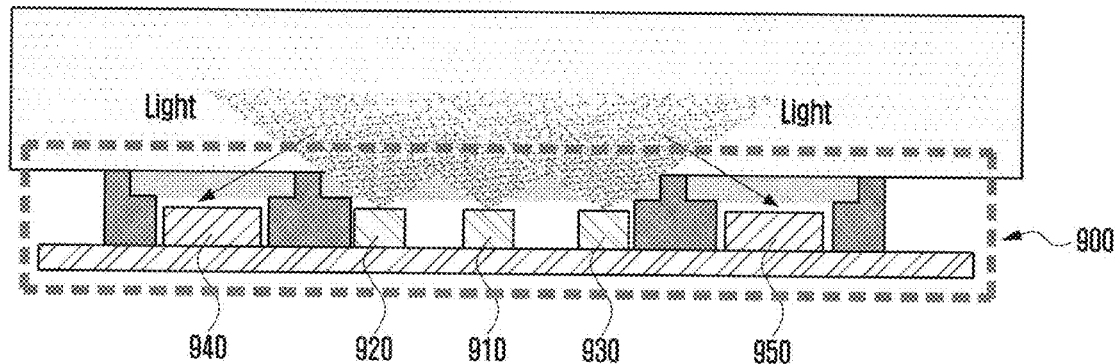

FIGS. 9A-9C are cross-sectional views illustrating a structure of an optical sensor 900 according to various embodiments.

According to various embodiments, a light emitting unit of the optical sensor 900 may include a plurality of light emitting elements. The plurality of light emitting elements may include light emitting elements having at least two identical wavelengths or may include light emitting elements that output at least two kinds of different wavelengths. For example, the light emitting unit may include a first light emitting element 910, second light emitting element 920, and third light emitting element 930.

According to various embodiments, the optical sensor 900 may include at least two light receiving units. For example, the optical sensor 900 may include a first light receiving unit 940 and a second light receiving unit 950.

According to various embodiments, the light emitting unit of the optical sensor 900 may be disposed in a structure enclosed by at least two light receiving units. For example, the light emitting unit may be disposed between the first light receiving unit 940 and the second light receiving unit 950.

According to various embodiments, a processor of an electronic device may select at least one light emitting element of a plurality of light emitting elements based on at least some of user information related to a living body and control to the light emitting element to output light through the at least one selected first light emitting element. For example, FIG. 9A illustrates a case of selecting the first light emitting element 910 of a plurality of light emitting elements and controlling the first light emitting element 910 to output light. In another example, FIG. 9B illustrates a case of selecting a second light emitting element 920 and a third light emitting element 930 of the plurality of light emitting elements and controlling the second light emitting element 920 and the third light emitting element 930 to simultaneously output light. In another example, FIG. 9C illustrates a case of selecting a first light emitting element 910, second light emitting element 920, and third light emitting element 930 of the plurality of light emitting elements and controlling the first light emitting element 910, the second light emitting element 920, and the third light emitting element 930 to output light.

According to various embodiments, adjacent light emitting elements may be spaced apart from each other in a designated distance range based on a radiation area of a designated range related to the light emitting unit. For example, each of the light emitting elements may be spaced apart from each other within a predetermined distance so as to affect both the first light receiving unit 940 and the second light receiving unit 950. According to an embodiment, the first light emitting element 910 and the second light emitting element 920 may be spaced apart from each other by a range of 0.5 mm to 2.1 mm as a designated distance range.

According to various embodiments, each light emitting element may have an emission angle of at least 70°. For example, when the light emitting elements are positioned apart from each other in a designated distance range, a radiation area may be reduced. According to various embodiments, each light emitting element may be configured to have an emission angle of at least 70° in order to form a large radiation area. According to some embodiments, each light emitting element may have an emission angle of at least 70° in order to affect both the first light receiving unit 940 and the second light receiving unit 950.

According to various embodiments, each of the plurality of light emitting elements may be configured to have different emission angles based on a radiation area of a designated range related to the light emitting unit. For example, the first light emitting element 910 may be configured to have a larger emission angle than that of the second light emitting element 920 and the third light emitting element 930 in order to affect both the first light receiving unit 940 and the second light receiving unit 950. The opposite case may also be present according to the embodiment.

Figure 10C:
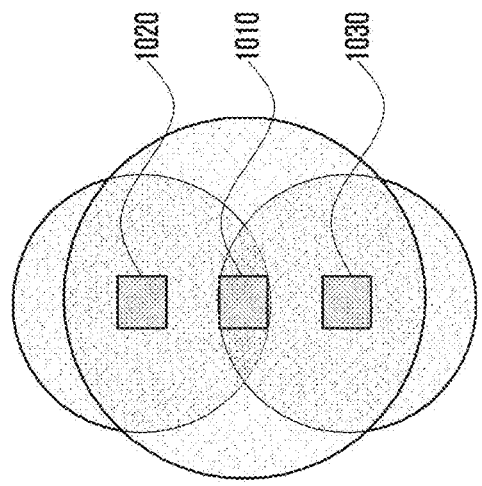
FIGS. 10A-10C are diagrams illustrating a light emitting unit according to various embodiments.
Figure 10B:
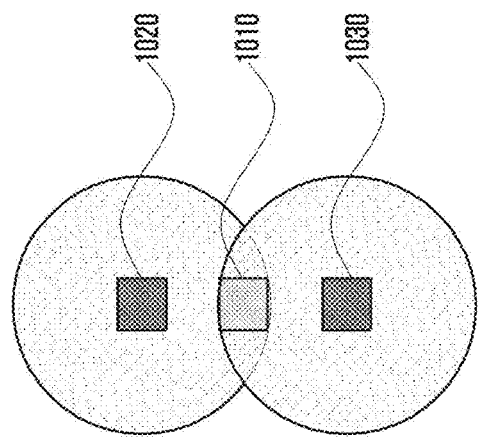
Figure 10A:
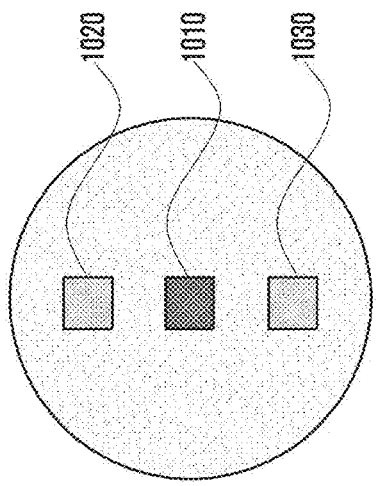

FIGS. 10A-10C are diagrams illustrating a light emitting unit according to various embodiments.

According to various embodiments, a light emitting unit including a plurality of light emitting elements may be configured with light emitting elements having different emission angles in order to form a radiation area of a predetermined range.

For example, FIG. 10A illustrates a case in which a first light emitting element 1010 disposed between a second light emitting element 1020 and a third light emitting element 1030 outputs light. The first light emitting element 1010 may be configured to have a wider angle than that of the second light emitting element 1020 and the third light emitting element 1030. For example, the first light emitting element 1010 may have an emission angle of 120°.

FIG. 10B illustrates a case in which a second light emitting element 1020 and a third light emitting element 1030 output light. The second light emitting element 1020 and the third light emitting element 1030 may be configured to have a smaller light angle than that of a first light emitting element 1010 in order to form a radiation area in a predetermined range of the optical sensor. For example, the second light emitting element 1020 and the third light emitting element 1030 may have an emission angle of 100°.

FIG. 10C illustrates a case in which a first light emitting element 1010, second light emitting element 1020, and third light emitting element 1030 output light. A radiation area formed by the first light emitting element 1010, the second light emitting element 1020, and the third light emitting element 1030 may form a radiation area of a designated range.

Figure 11C:
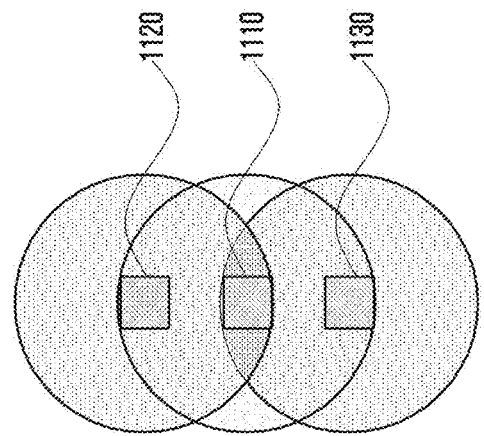
FIGS. 11A-11C are diagrams illustrating a light emitting unit according to various embodiments.
Figure 11B:
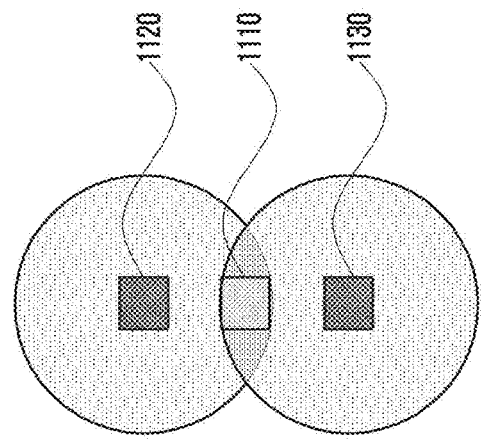
Figure 11A:
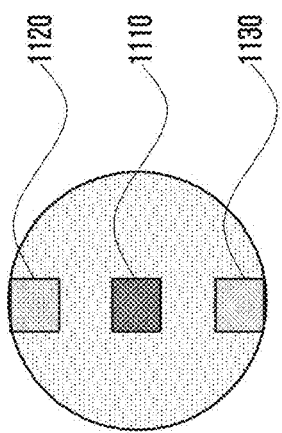

FIGS. 11A-11C are diagrams illustrating a light emitting unit according to various embodiments.

When light emitting elements that output the same wavelength band are disposed adjacent to each other, some of a radiation area formed by each of the light emitting elements may be overlapped. Because a relatively large amount of light is transmitted to the overlapping radiation area, by adjusting an intensity of a current transferred to each of the light emitting elements so that the entire radiation area has uniform brightness, the entire radiation area may have relatively uniform brightness.

FIG. 11A illustrates a case of outputting light to only a first light emitting element 1110. In this case, there is no radiation area overlapping by other light emitting elements, and a radiation area formed by the first light emitting element 1110 may have uniform brightness.

FIG. 11B illustrates a case in which a second light emitting element 1120 and a third light emitting element 1130 simultaneously output light. A radiation area formed by the second light emitting element 1120 and the third light emitting element 1130 may include some overlapped areas. However, the some overlapped area may be negligibly small.

FIG. 11C illustrates a case in which the first light emitting element 1110, the second light emitting element 1120, and the third light emitting element 1130 simultaneously output light. It may be determined that most of a radiation area formed by the first light emitting element 1110 overlaps with a radiation area formed by the second light emitting element 1120 or the third light emitting element 1130. In this case, a current value smaller than that supplied to the second light emitting element 1120 and the third light emitting element 1130 may be supplied to the first light emitting element 1110 so that the entire radiation area may have relatively uniform brightness. For example, a current of 10 mA may be supplied to the first light emitting element 1110, and a current of 20 mA may be supplied to each of the second light emitting element 1120 and the third light emitting element 1130.

Figure 12A:
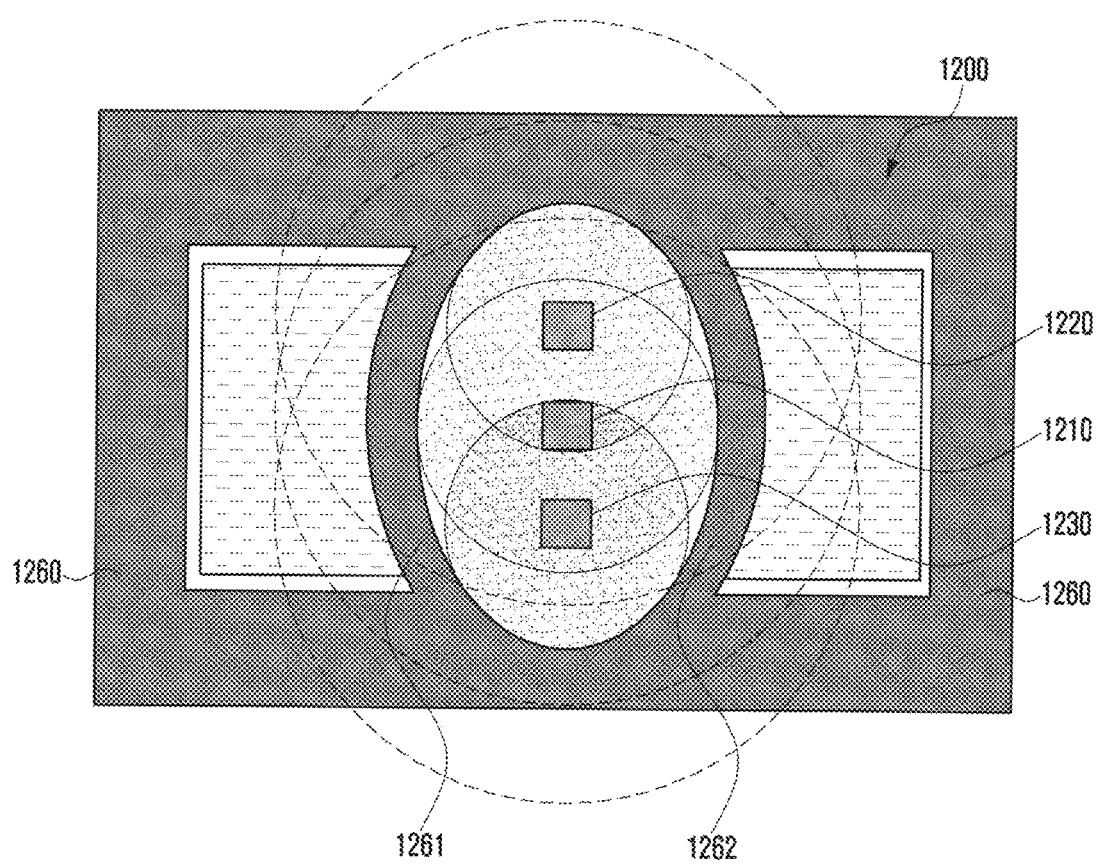
FIGS. 12A and 12B are diagrams illustrating an optical sensor according to various embodiments.
Figure 12B:
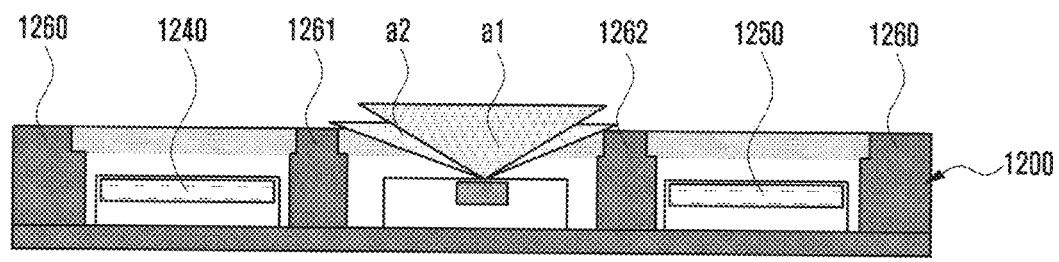

FIGS. 12A and 12B are diagrams illustrating an optical sensor 1200 according to various embodiments.

According to various embodiments, a light emitting unit including a plurality of light emitting elements may be configured with light emitting elements having different emission angles in order to form a radiation area of a predetermined range. For example, with reference to FIG. 12A representing a front view of the optical sensor 1200, a first light emitting element 1210 disposed between a second light emitting element 1220 and a third light emitting element 1230 may have a wider angle than that of the second light emitting element 1220 and the third light emitting element 1230. For example, the first light emitting element 1210 may have an emission angle of 120°, and the second light emitting element 1220 and the third light emitting element 1230 may have an emission angle of 100°. With reference to FIG. 12B representing a side view of the optical sensor 1200, the first light emitting element 1210 may have a wide angle of a2 and the second light emitting element 1220 and the third light emitting element 1230 may have a wide angle of a1.

A radiation area formed by each of the plurality of light emitting elements may have a substantially circular shape. For example, the first light emitting element 1210 having a relatively large emission angle may form a relatively large circular radiation area, and the second light emitting element 1220 and the third light emitting element 1230 may form a relatively small circular radiation area.

According to various embodiments, the light emitting unit may be formed in a structure enclosed by the first light receiving unit 1240 and the second light receiving unit 1250.

According to various embodiments, the optical sensor may further include a barrier rib to prevent light output from the light emitting unit or light around the optical sensor from being directly applied to the first light receiving unit 1240 or the second light receiving unit 1250. For example, in order to prevent some of light output by the light emitting unit from being directly applied to the first light receiving unit 1240 or the second light receiving unit 1250 without passing through a living body or in order to prevent some of light output by the light emitting unit from being directly applied to the first light receiving unit 1240 or the second light receiving unit 1250 by reflecting from a surface of the optical sensor or a surface of the living body, the optical sensor may include first barrier ribs (e.g., a first barrier rib 1261 and a first barrier rib 1262) disposed between the light receiving unit and the light emitting unit.

According to various embodiments, the first barrier ribs (e.g., the first barrier rib 1261 and the first barrier rib 1262) may be formed to correspond to at least radiation area formed by each of the plurality of light emitting elements. For example, the first barrier ribs (e.g., the first barrier rib 1261 and the first barrier rib 1262) may be formed in a convex shape including all radiation areas formed by each of the plurality of light emitting elements. For example, the first barrier rib may be formed in a convex shape including both a relatively large circular radiation area formed by the first light emitting element 1210 and a relatively small circular radiation area formed by the second light emitting element 1220 and the third light emitting element 1230.

According to various embodiments, in order to prevent light around the optical sensor from being applied directly to the first light receiving unit 1240 or the second light receiving unit 1250, the optical sensor 1200 may include a second barrier rib 1260 disposed between the first light receiving unit 1240 or the second barrier rib 1260 and an external environment. According to various embodiments, shapes of the barrier rib may be formed in various shapes according to the purpose of the barrier rib, a structure of the device, and the like.

Figure 13:
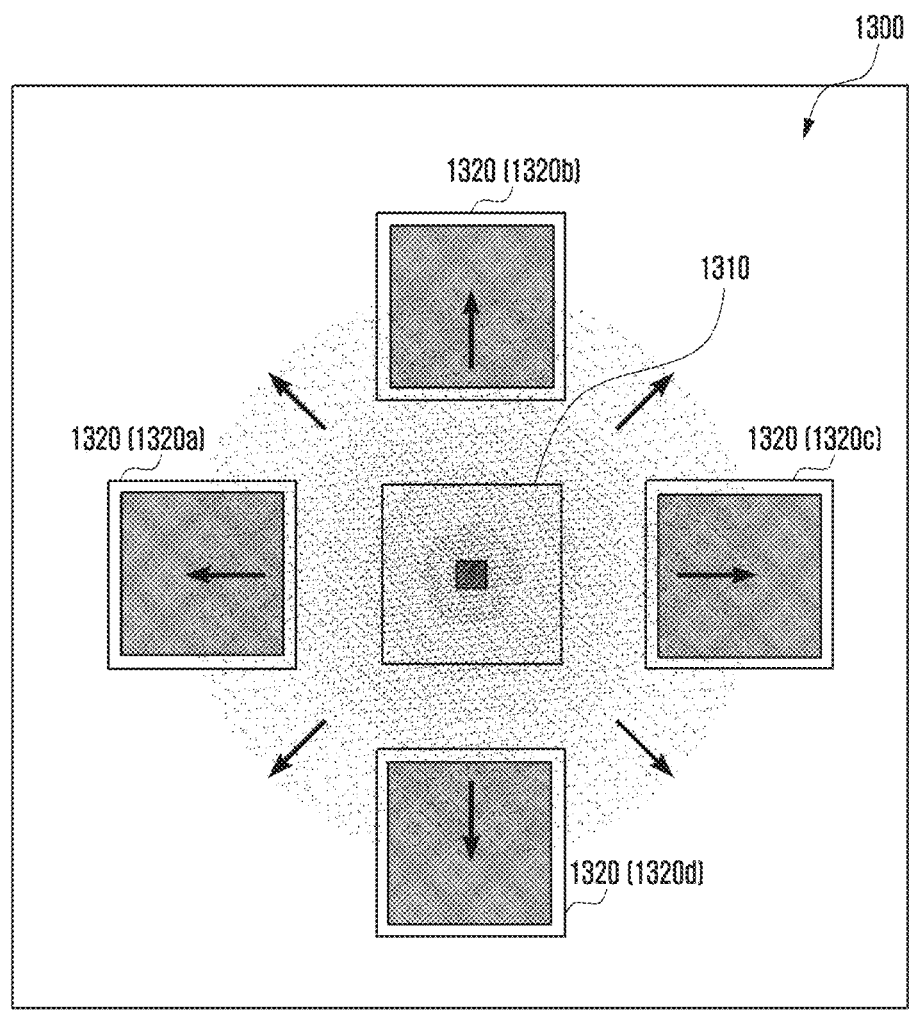
FIG. 13 is a diagram illustrating an optical sensor according to various embodiments.

FIG. 13 is a diagram illustrating an optical sensor 1300 according to various embodiments.

According to various embodiments, the optical sensor 1300 may include a plurality of light receiving units 1320. For example, the optical sensor 1300 may include a first light receiving unit 1320a, second light receiving unit 1320b, third light receiving unit 1320c, and fourth light receiving unit 1320d.

According to various embodiments, the plurality of light receiving units may be disposed to enclose a light emitting unit 1310. For example, the plurality of light receiving units (e.g., a first light receiving unit 1320a, second light receiving unit 1320b, third light receiving unit 1320c, and fourth light receiving unit 1320d) on a virtual circle enclosing the light emitting unit 1310 may be spaced apart from each other by a predetermined distance.

An electronic device according to various embodiments of the present disclosure includes a light emitting unit including a first light emitting element and a second light emitting element; and a plurality of light receiving units disposed in a structure that encloses the light emitting unit, wherein the first light emitting element and the second light emitting element are disposed in a separated state based on a radiation area related to the light emitting unit in a designated distance range.

According to various embodiments of the present disclosure, the designated distance range may include a range of 0.5 mm to 2.1 mm.

According to various embodiments of the present disclosure, the first light emitting element and the second light emitting element may have an emission angle of at least 70°.

According to various embodiments of the present disclosure, the first light emitting element and the second light emitting element may have different emission angles.

According to various embodiments of the present disclosure, the electronic device may further include at least two barrier ribs disposed between each of the plurality of light receiving units and the light emitting unit, wherein the at least two barrier ribs may be formed in a shape at least corresponding to the radiation area.

Figure 14:
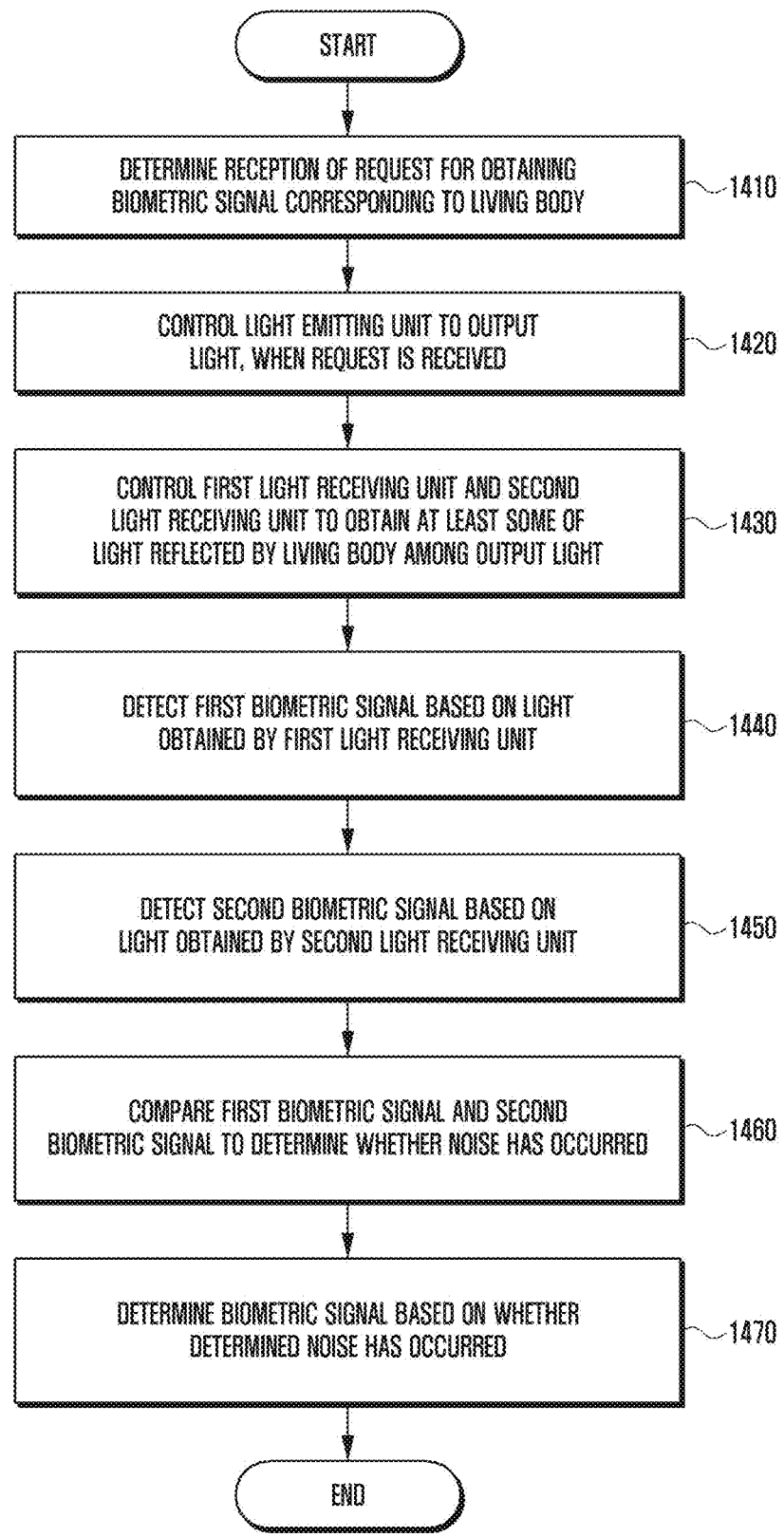
FIG. 14 is a flowchart illustrating a method of controlling an electronic device including an optical sensor according to various embodiments.

FIG. 14 is a flowchart illustrating a method of controlling an electronic device including an optical sensor according to various embodiments.

At operation 1410, the processor 210 of the electronic device 200 may determine reception of a request for obtaining a biometric signal corresponding to a living body. For example, the processor 210 may perform substantially the same operations as operation 611 of FIG. 6A or operation 621 of FIG. 6B.

At operation 1420, when receiving the request, the processor 210 of the electronic device 200 may control the light emitting unit to output light.

According to various embodiments, the light emitting unit may include at least one light emitting element. For example, the processor 210 of the electronic device 200 may select one or more light emitting elements of at least one light emitting element based on at least some of user information related to a living body and control the light emitting unit to output light through the selected one or more light emitting elements. According to an embodiment, the processor 210 of the electronic device 200 may determine a wavelength of light based on at least some of user information related to the living body, select one or more light emitting elements of at least one light emitting element based on the determined light wavelength, and control to output light through the selected one or more light emitting elements.

At operation 1430, the processor 210 of the electronic device 200 may control a first light receiving unit and a second light receiving unit to obtain at least some of light reflected by the living body among the output light.

For example, when light is output directly to a user's skin, the user's skin may emit again some of light outside thereof. In this case, some of the light output again outside the user's skin may be obtained through the first light receiving unit and the second light receiving unit.

At operation 1440, the processor 210 may detect a first biometric signal based on at least some of the light obtained by the first light receiving unit.

The first biometric signal, for example, some of the light output again outside the skin may include at least one of a direct current (DC) component that returns to a predetermined size by a skin, tissue, pigment, etc., a venous blood DC component by absorption or reflection of venous blood of capillaries, an arterial blood DC component by absorption or reflection of arterial blood of capillaries, and AC component by arterial blood.

At operation 1450, the processor 210 of the electronic device 200 may detect a second biometric signal based on at least some of second light obtained by the second light receiving unit.

According to various embodiments, the second biometric signal may include the same component as that contained in the first biometric signal. For example, when the first biometric signal includes an AC component by arterial blood, the second biometric signal may include an AC component by arterial blood.

FIG. 14 illustrates that operations 1440 and 1450 are performed sequentially, but operations 1440 and 1450 may be performed simultaneously by one processor 210 or two or more processors 210. Further, the order of operations may be mutually changed.

At operation 1460, the processor 210 of the electronic device 200 may compare the first biometric signal and the second biometric signal to determine whether noise has occurred.

Noise may occur based on various causes such as user breathing, motion artifact, and peripheral noise (e.g., influx of external light).

According to various embodiments, the first biometric signal and the second biometric signal may include substantially the same component. Therefore, when the first and second biometric signals representing the same component show a large difference, it may be determined that noise occurs in at least one signal. For example, at a specific segment, when the first biometric signal shows an abrupt change, but when the second biometric signal does not include such a sudden change, the processor 210 of the electronic device 200 may determine that a noise component is included at the specific segment of the first biometric signal.

According to various embodiments, the electronic device may further include a sensor module 230 that may detect a moving state. For example, the processor 210 of the electronic device 200 may determine a moving state of the electronic device 200 using the sensor module 230 (e.g., an acceleration sensor). Further, the processor 210 of the electronic device 200 may predict that biometric signals will include motion artifact based on the determined motion state of the electronic device 200.

At operation 1470, the processor 210 of the electronic device 200 may determine the biometric signal based on whether the determined noise has occurred.

According to various embodiments, the processor 210 of the electronic device 200 may select a biometric signal determined to be less affected by noise among the first biometric signal and the second biometric signal or may perform correction that removes the determined noise from a particular biometric signal. For example, when the first biometric signal shows a sudden change at a specific segment, the processor 210 may determine that a noise component is contained at the specific segment of the first biometric signal and obtain a biometric signal based on the second biometric signal. Further, the processor 210 may analyze noise from the first biometric signal and compensate the analyzed noise from the second biometric signal to obtain an accurate biometric signal.

According to an embodiment, the processor 210 of the electronic device 200 may select a light receiving unit that has the least influence on motion artifact based on a moving state of the electronic device 200 determined by the acceleration sensor. For example, the electronic device 200 including a plurality of light receiving units may dispose light receiving units in various disposition structures. Due to such a disposition structure, the light receiving unit may be much affected or may be less affected by a movement in a specific direction. When a movement in a specific direction is detected, the processor 210 of the electronic device 200 may select a light receiving unit expected to be the least affected by the movement. Further, the processor 210 of the electronic device 200 may obtain a biometric signal based on the selected light receiving unit.

FIGS. 15 to 18 are graphs and diagrams illustrating examples in which an electronic device determines motion artifact according to various embodiments.

Figure 15:
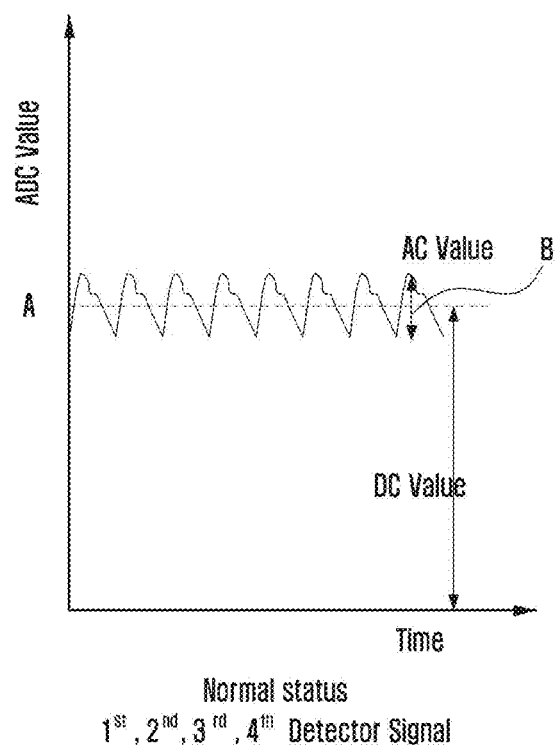

FIG. 15 illustrates an example of a biometric signal (hereinafter, referred to as a 'normal state') when a noise component is not included. The normal state may mean a state in which a noise component is not included, such as when the user maintains a sleep state or a static state. In this case, the plurality of light receiving units (e.g., a first light receiving unit, second light receiving unit, third light receiving unit, and fourth light receiving unit) may obtain biometric signals of the same value or similar values. For example, a plurality of light receiving units may obtain a biometric signal having an amplitude A with a DC value and an amplitude B with an AC value.

Figure 16A:
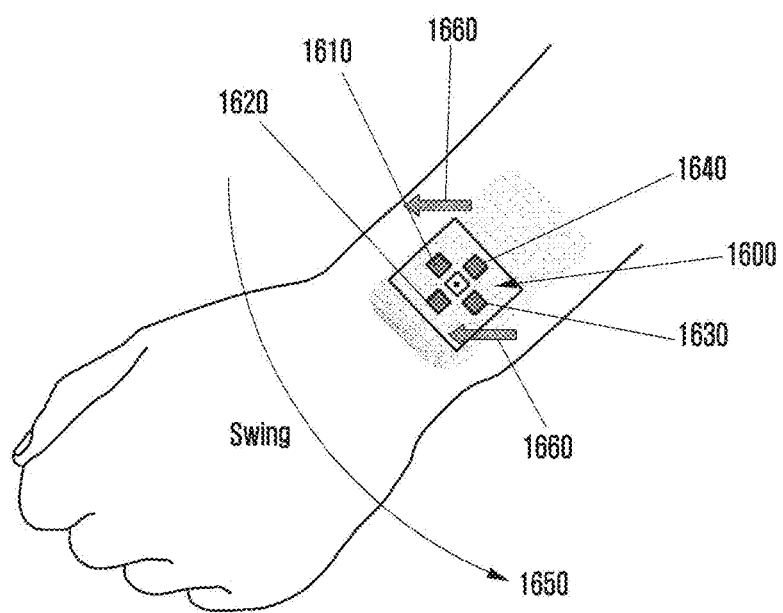
Figure 16B:
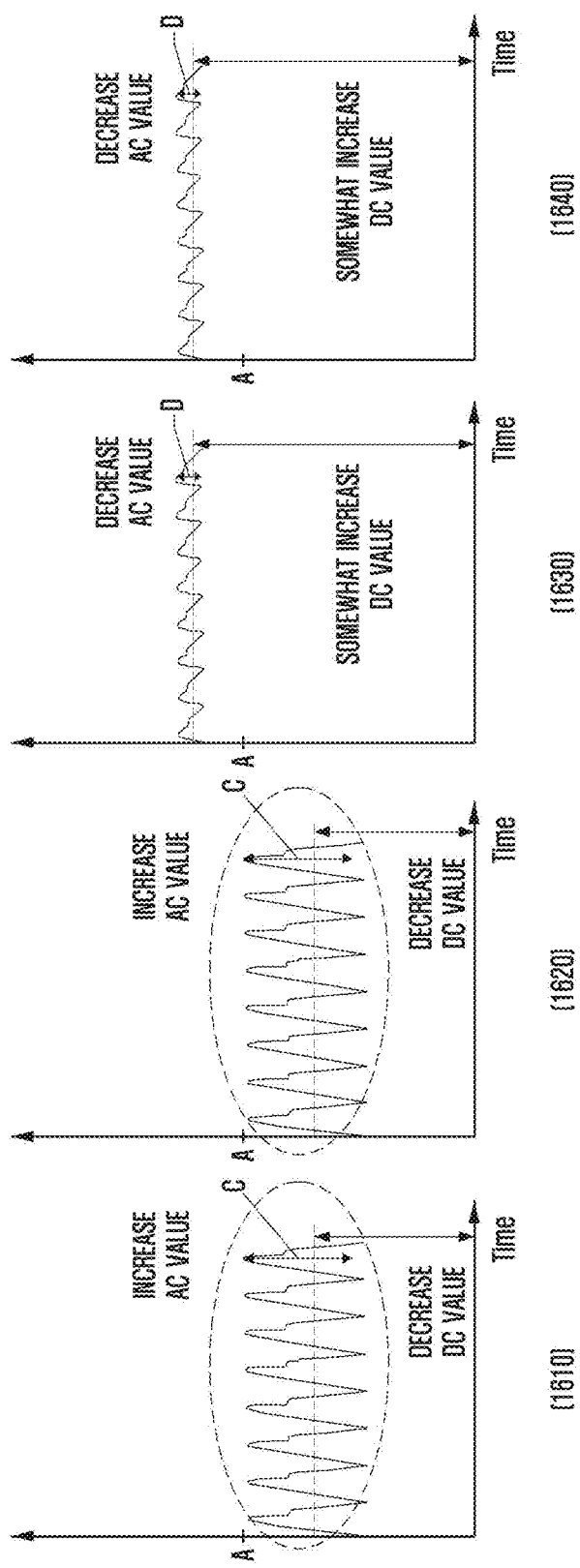

FIGS. 16A to 16B illustrate a case in which motion artifact occurs. For example, when a user wearing an electronic device 1600 on his/her wrist is walking or jogging, the biometric signal may include motion artifact according to a movement of the user.

FIG. 16A illustrates a case in which the user moves in a direction 1650. In this case, the blood inside the user's skin may be leaned in a direction 1660, which is a direction opposite to that of the user's movement according to the law of inertia. FIG. 16B illustrates an influence of biometric signals due to a movement of the blood. For example, in biometric signals obtained by first and second light receiving units 1610 and 1620, it may be determined that a DC value is lower than A and that an AC value is increased from an amplitude B to an amplitude C. Further, in biometric signals obtained by a third light receiving unit 1630 and a fourth light receiving unit 1640, it may be determined that a DC value is higher than A and that an AC value is decreased from the amplitude B to the amplitude D.

Figure 17A:
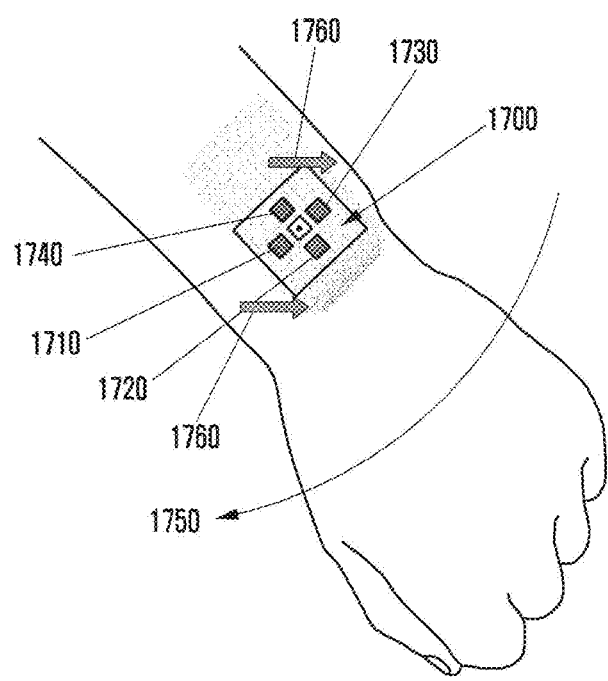
Figure 17B:
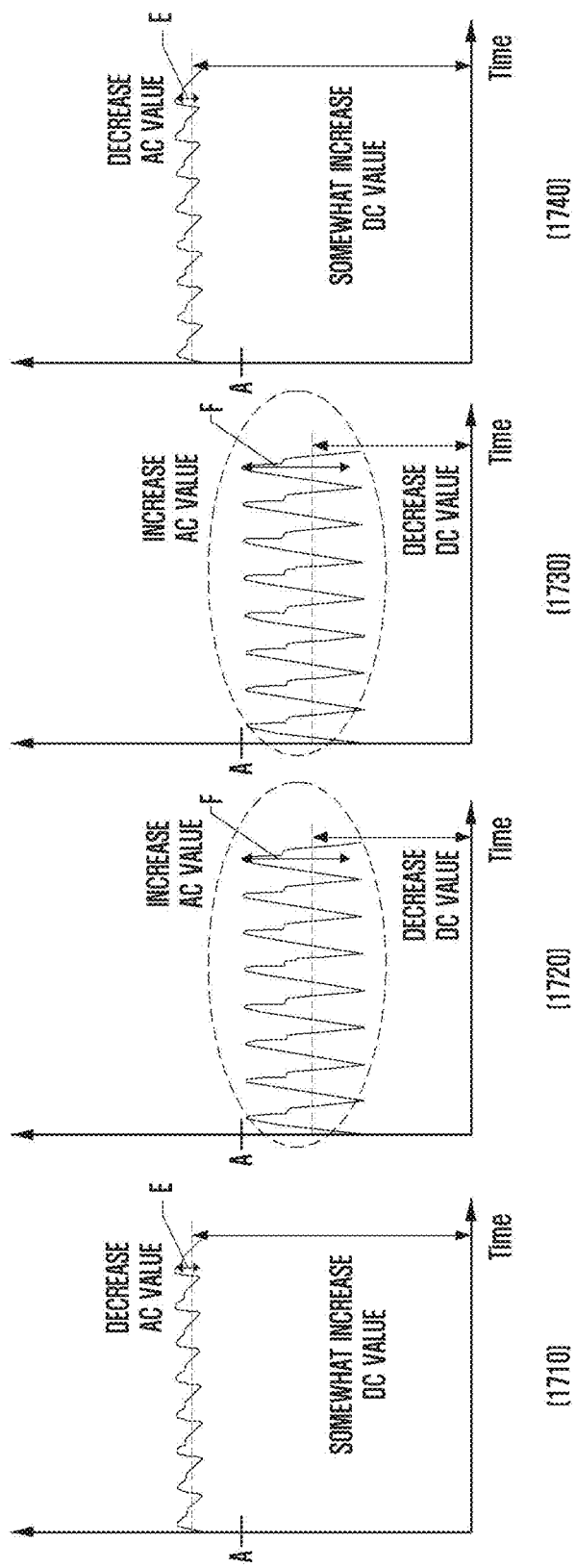

FIGS. 17A to 17B illustrate examples in which motion artifact occurs. For example, when a user wearing an electronic device 1700 on his/her wrist is walking or jogging, a situation opposite to the situation illustrated in FIGS. 16A and 16B may occur alternatively.

FIG. 17A illustrates a case in which the user moves in a direction 1750. Similarly, the blood inside the user's skin may be leaned in a direction 1760, which is a direction opposite to that of the user's movement according to the law of inertia. FIG. 17B illustrates an influence of a biometric signal due to a movement of the blood. For example, in biometric signals obtained by a first light receiving unit 1710 and a fourth light receiving unit 1740, it may be determined that a DC value is higher than A and that an AC value is decreased from an amplitude B to an amplitude E. Further, in biometric signal obtained by a second light receiving unit 1720 and a third light receiving unit 1730, it may be determined that a DC value is lower than A and that an AC value is increased from an amplitude B to an amplitude F.

FIG. 18 illustrates an embodiment of predicting occurrence of motion artifact and removing the predicted motion artifact from a biometric signal.

For example, the processor 210 of the electronic device 200 may determine the user's moving state based on a sensor module (e.g., an acceleration sensor). For example, the processor 210 of the electronic device 200 may determine that the user is walking or jogging based on the sensor module and predict occurrence of motion artifact, as illustrated in FIGS. 16A-17B.

For example, the processor 210 of the electronic device 200 may predict that a fourth light receiving unit D4 will have the least influence on motion artifact based on information obtained from the acceleration sensor. It may be also predicted that a first light receiving unit D1 and a third light receiving unit D3 will be most affected by motion artifact. The processor 210 of the electronic device 200 may analyze information related to motion artifact from the biometric signals obtained by the first light receiving unit D1 and the third light receiving unit D3 based on such prediction. Further, when the analyzed motion artifact is removed from the biometric signal obtained by the fourth light receiving unit D4, a biometric signal may be obtained in which the motion artifact is removed.

Figure 19A:
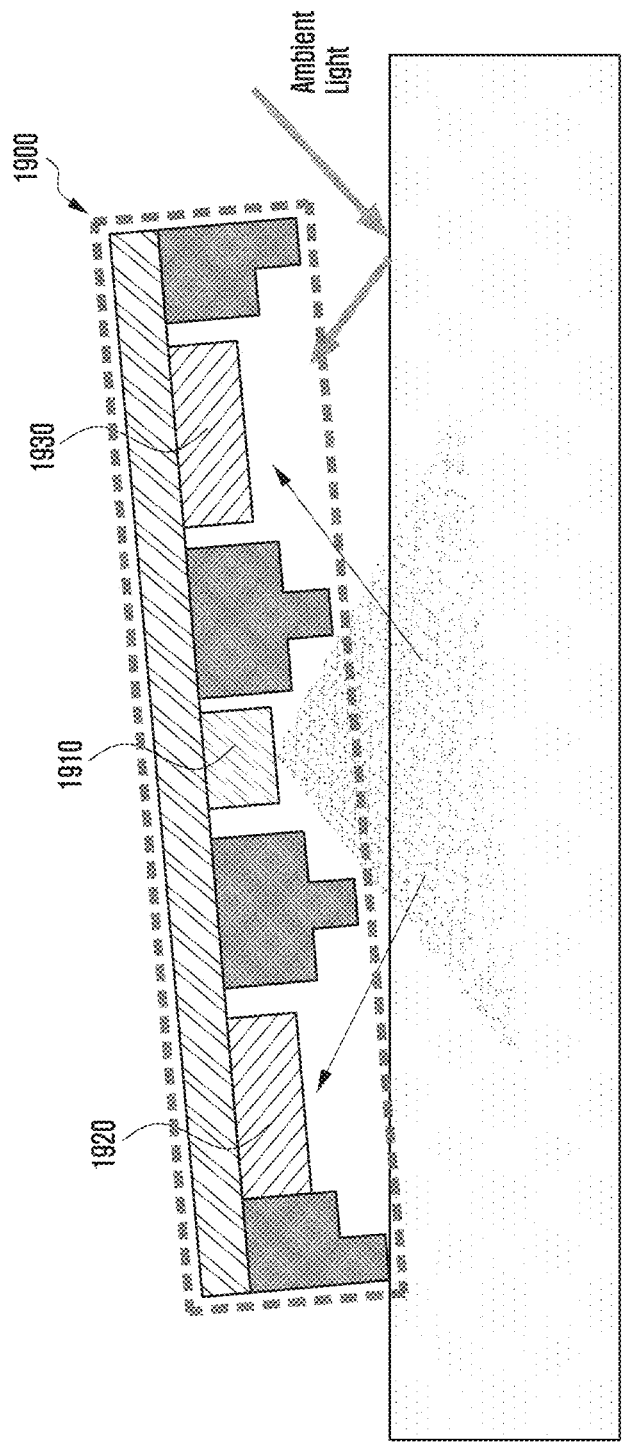
FIGS. 19A and 19B are diagrams illustrating an example in which an electronic device determines peripheral noise according to various embodiments.
Figure 19B:
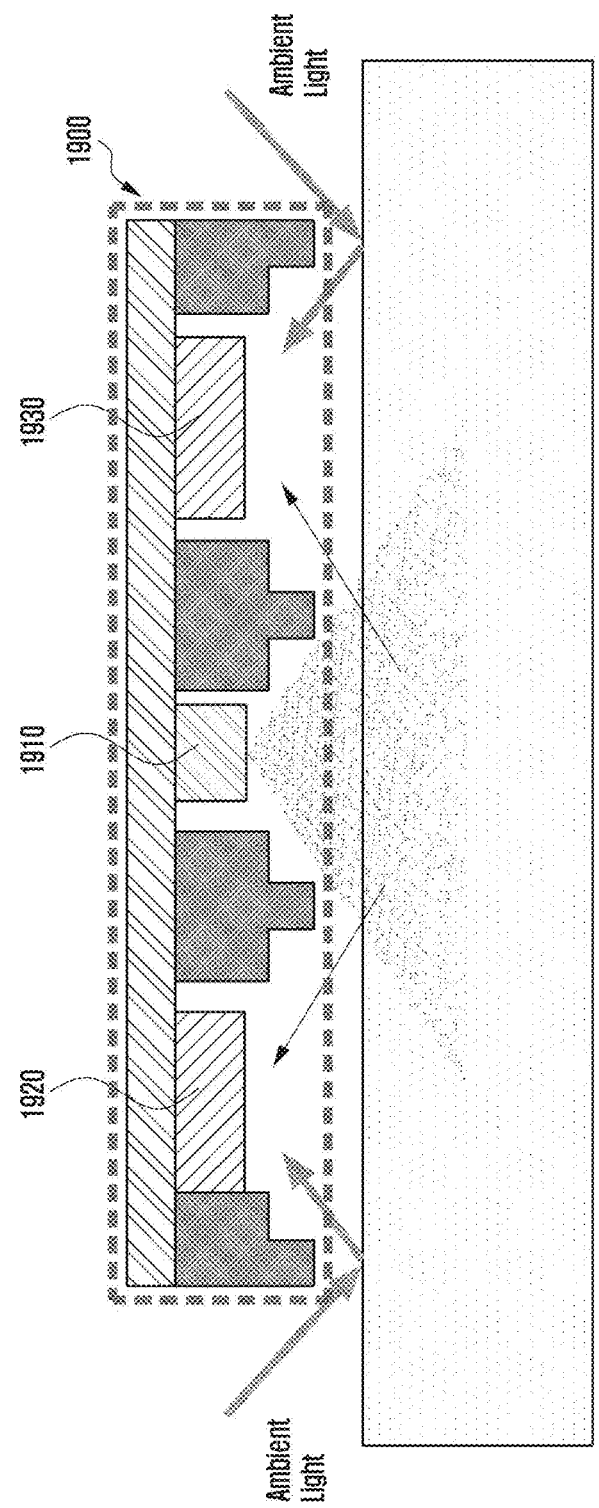

FIGS. 19A and 19B are diagrams illustrating an example in which an electronic device 1900 determines peripheral noise according to various embodiments.

According to various embodiments, in order to prevent light around the optical sensor from being directly applied to a first light receiving unit 1920 or a second light receiving unit 1930, the electronic device 1900 may include a second barrier rib disposed between the first light receiving unit 1240 or the light receiving unit 1250 and an external environment. Although the electronic device 1900 includes such a second barrier rib, the electronic device 1900 may not completely block peripheral light. For example, peripheral light may be directly applied to the first light receiving unit 1240 or the second light receiving unit 1250 according to a user's movement, a wearing state, or an intensity of peripheral light. For example, at a day of strong sunlight, when the user wears the electronic device 200 on his/her wrist and walks or jogs, the user may be exposed periodically to the shade or sunlight. When the user is exposed to sunlight, peripheral light penetrates to the user's skin and is diffused, and some of the light penetrated to the skin may be applied to the first light receiving unit 1240 or the second light receiving unit 1250 at a position of the light receiving unit. Further, even if the user is under the shade of a tree, the degree of exposure to sunlight because of shaking of leaves by the wind may be continuously changed and have an influence on biometric signals obtained by the first light receiving unit 1240 or the second light receiving unit 1250.

According to various embodiments, the electronic device 1900 including a plurality of light receiving units may compare biometric signals obtained from each light receiving unit to determine whether noise (e.g., peripheral noise) has occurred and select a biometric signal in which an influence of noise is determined to be small or perform correction that removes the determined noise from a specific signal.

FIG. 19A illustrates a case in which peripheral noise occurs. For example, the electronic device 1900 including the first light receiving unit 1920 and the second light receiving unit 1930 may come in partial indirect contact with the user's skin because of a user's movement or external factors. External light may penetrate through such an indirect contact portion. For example, the second light receiving unit 1930 may obtain both lights output from a light emitting unit 1910 and external light. Because the first light receiving unit 1920 is not affected by external light, the first light receiving unit 1920 may obtain only light output by the light emitting unit. The processor 210 of the electronic device 200 may compare biometric signals obtained by the first light receiving unit 1920 and the second light receiving unit 1930 and determine whether peripheral noise occurs. For example, the processor 210 may detect that a sudden change has occurred at a specific segment of the biometric signal obtained by the second light receiving unit 1930 and compare the biometric signal with the biometric signal obtained by the first light receiving unit 1920 to determine whether peripheral noise occurs. The electronic device 1900 may select a biometric signal obtained by the first light receiving unit 1920 or determine noise from a biometric signal obtained by the second light receiving unit 1930 to correct the biometric signal obtained by the first light receiving unit 1920, thereby obtaining a biometric signal in which noise is removed.

FIG. 19B illustrates a case in which peripheral noise occurs. For example, it may mean that peripheral noise is introduced into both the first light receiving unit and the second light receiving unit while the electronic device 200 comes in indirect contact with the user's skin (e.g., a separation phenomenon occurs). In such a case, it may be very difficult to obtain an accurate biometric signal. However, the electronic device 1900 may compare biometric signals obtained by the first light receiving unit 1920 and the second light receiving unit 1930 and remove some noise.

The electronic device according to various embodiments may be one of various types of electronic devices. The electronic devices may include, for example, a portable communication device (e.g., a smartphone), a computer device, a portable multimedia device, a portable medical device, a camera, a wearable device, or a home appliance. According to an embodiment of the disclosure, the electronic devices are not limited to those described above.

It should be appreciated that various embodiments of the present disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include any one of, or all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), it means that the element may be coupled with the other element directly (e.g., wiredly), wirelessly, or via a third element.

As used herein, the term "module" may include a unit implemented in hardware, software, or firmware, and may interchangeably be used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

Various embodiments as set forth herein may be implemented as software (e.g., the program 140) including one or more instructions that are stored in a storage medium (e.g., internal memory 136 or external memory 138) that is readable by a machine (e.g., the electronic device 101). For example, a processor (e.g., the processor 120) of the machine (e.g., the electronic device 101) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a complier or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment, a method according to various embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., PlayStore™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments, each component (e.g., a module or a program) of the above-described components may include a single entity or multiple entities. According to various embodiments, one or more of the above-described components may be omitted, or one or more other components may be added. Alternatively or additionally, a plurality of components (e.g., modules or programs) may be integrated into a single component. In such a case, according to various embodiments, the integrated component may still perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

An electronic device according to various embodiments of the present disclosure can reduce a consumption current of an optical sensor to be used for measuring a biometric signal and measure a more accurate biometric signal.

An electronic device according to various embodiments of the present disclosure can compensate for peripheral noise or motion artifact occurring according to motion and wearing states.

Although embodiments of the present disclosure have been described in detail hereinabove, it should be clearly understood that many variations and modifications of the basic inventive concepts herein described, which may appear to those skilled in the art, will still fall within the spirit and scope of the embodiments of the present disclosure as defined in the appended claims.

Although the present disclosure has been described with various embodiments, various changes and modifications may be suggested to one skilled in the art. It is intended that the present disclosure encompass such changes and modifications as fall within the scope of the appended claims.

What is claimed is:

1. An electronic device, comprising:
    a light emitting unit comprising a plurality of first light emitting elements configured to output first light including a first wavelength;
    a first light receiving unit and a second light receiving unit, each of the first and second light receiving units comprising at least one of a photodiode or a pyroelectric detector;
    one or more sensors; and
    a processor configured to:
        control to receive a request for obtaining a biometric signal corresponding to a living body;

select, when the request is received, at least one first light emitting element of the plurality of first light emitting elements based on user information related to the living body;

control the light emitting unit to output light through the selected at least one first light emitting element;

adjust an intensity of a current transferred to at least one first light emitting element which corresponds to an overlapping radiation area formed by the plurality of first light emitting elements;

control the first light receiving unit and the second light receiving unit to receive at least some of light reflected by the living body among the output light;

detect a first biometric signal based on the light received by the first light receiving unit;

detect a second biometric signal based on the light received by the second light receiving unit;

compare the first biometric signal and the second biometric signal to determine whether noise comprising at least one of a motion artifact or peripheral noise has occurred; and determine the requested biometric signal based on whether the noise has occurred, wherein the processor is further configured to:

determine a moving state of the electronic device using the one or more sensors;

predict whether the motion artifact has occurred based on the determined moving state of the electronic device; and determine the requested biometric signal by removing the predicted motion artifact from at least one of the first biometric signal or the second biometric signal.

2. The electronic device of claim 1, wherein each of the plurality of first light emitting elements has an output intensity of a designated range.

3. The electronic device of claim 2, wherein the processor is further configured to:

select, when the request is received, the at least one first light emitting element of the plurality of first light emitting elements having the output intensity of the designated range such that the selected at least one first light emitting element has an output intensity sufficient for obtaining the requested biometric signal.

4. The electronic device of claim 1, further comprising a user interface configured to receive a user input, wherein the processor is further configured to:

control the user interface to receive the user information related to the living body;

determine characteristics of the living body based on user information related to the living body; and select the at least one first light emitting element of the plurality of first light emitting elements based on the determined characteristics of the living body.

5. The electronic device of claim 1, wherein the processor is further configured to:

control to receive, from an external device, the user information related to the living body;

determine characteristics of the living body based on user information related to the living body; and select the at least one first light emitting element of the plurality of first light emitting elements based on the determined characteristics of the living body.

6. The electronic device of claim 1, wherein the processor is configured to control to receive the request for obtaining the biometric signal based on an occurrence of an event previously set by a user or an event according to a user's health state.

7. The electronic device of claim 1, wherein the user information related to the living body comprises at least one of user age, sex, genetic information, or hospital treatment history.

8. The electronic device of claim 1, further comprising one or more sensors configured to determine situation information related to the electronic device, wherein the processor is configured to:

control the one or more sensors to determine the situation information; and select the at least one first light emitting element of the plurality of first light emitting elements based on the situation information.

9. The electronic device of claim 8, wherein the situation information comprises at least one of motion information, exercise information, or position information of a user.

10. The electronic device of claim 1, wherein the processor is configured to select the at least one first light emitting element of the plurality of first light emitting elements based on information of the electronic device.

11. The electronic device of claim 10, wherein the information of the electronic device comprises at least one of battery information or information of a running application.

12. An electronic device, comprising:

a light emitting unit comprising:

at least one first light emitting element configured to output first light including a first wavelength, and at least one second light emitting element configured to output second light including a second wavelength;

a first light receiving unit and a second light receiving unit, each of the first and second light receiving units comprising at least one of a photodiode or a pyroelectric detector;

one or more sensors; and a processor configured to:

control to receive a request for obtaining a biometric signal corresponding to a living body;

determine, when the request is received, a wavelength of light based on at least some of user information related to the living body;

select one or more light emitting elements of the at least one first light emitting element and of the at least one second light emitting element based on the determined light wavelength;

control the light emitting unit to output light through the selected one or more light emitting elements;

adjust an intensity of a current transferred to at least one of the at least one first light emitting element and the at least one second light emitting element which corresponds to an overlapping radiation area formed by the at least one first light emitting element and the at least one second light emitting element;

control the first light receiving unit and the second light receiving unit to receive at least some of light reflected by the living body among the output light;

detect a first biometric signal based on the light received by the first light receiving unit;

detect a second biometric signal based on the light received by the second light receiving unit;

compare the first biometric signal and the second biometric signal to determine whether noise comprising at least one of a motion artifact or peripheral noise has occurred; and determine the requested biometric signal based on whether the noise has occurred, wherein the processor is further configured to:

determine a moving state of the electronic device using the one or more sensors;

predict whether the motion artifact has occurred based on the determined moving state of the electronic device; and determine the requested biometric signal by removing the predicted motion artifact from at least one of the first biometric signal or the second biometric signal.

13. The electronic device of claim 12, wherein each of the at least one first light emitting element and the at least one second light emitting element has an output intensity of a designated range.

14. The electronic device of claim 13, wherein the processor is further configured to:

determine, when the request is received, an intensity of light based on determined characteristics of the living body; and select the one or more light emitting elements of the at least one first light emitting element and of the at least one second light emitting element based on the determined light wavelength and the determined light intensity.

* * * * *